US012591129B2

(12) United States Patent
Feinbloom et al.

(10) Patent No.: US 12,591,129 B2
(45) Date of Patent: Mar. 31, 2026

(54) MULTIPLE LIGHT SOURCE CONFIGURATION

(71) Applicant: Designs for Vision, Inc., Bohemia, NY (US)

(72) Inventors: Richard E. Feinbloom, New York, NY (US); Moty Solomon, Beit uziel (IL)

(73) Assignee: Designs for Vision, Inc., Bohemia, NY (US)

( * ) Notice: Subject to any disclaimer, the term of this patent is extended or adjusted under 35 U.S.C. 154(b) by 0 days.

(21) Appl. No.: 19/064,593

(22) Filed: Feb. 26, 2025

(65) Prior Publication Data

US 2025/0216668 A1 Jul. 3, 2025

Related U.S. Application Data

(63) Continuation-in-part of application No. 18/664,080, filed on May 14, 2024, now Pat. No. 12,416,801, (Continued)

(51) Int. Cl.
*G02B 25/02* (2006.01)
*A61B 5/00* (2006.01)
(Continued)

(52) U.S. Cl.
CPC ............ *G02B 25/02* (2013.01); *A61B 5/0017* (2013.01); *A61B 5/0077* (2013.01); (Continued)

(58) Field of Classification Search
CPC ...... G02B 25/02; G02B 5/208; G02B 25/004; G02B 25/008; A61B 90/30; A61B 90/35; (Continued)

(56) References Cited

U.S. PATENT DOCUMENTS 5,838,247 A 11/1998 Bladowski
8,272,762 B2* 9/2012 Maxik .................. H05K 1/0278
362/249.02
(Continued)

FOREIGN PATENT DOCUMENTS

DE 102007049345 7/2009
EP 3900608 10/2021
(Continued)

OTHER PUBLICATIONS

Extended European Search Report, issued Jun. 3, 2022.
(Continued)

*Primary Examiner* — Bryon T Gyllstrom
(74) *Attorney, Agent, or Firm* — Law Officde of Carl Giordano, PC

(57) ABSTRACT

A lighting assembly including a plurality of lighting sources or modules arranged concentrically about an inner circumference of the lighting device, wherein the plurality of lighting sources or modules emit light in at least one of a plurality of wavelength ranges (UV, visible (e.g., blue, green, yellow, orange, red, white, etc.), IR) onto a lighting director device that redirects the emitted light toward a lens system, wherein optical characteristics of the lens system being selected to focus the light onto a viewing point a known distance from the lighting assembly. Further disclosed is a passthrough within the lighting director device that allows light positioned on a base of the lighting device to pass through the lighting director.

20 Claims, 35 Drawing Sheets

Related U.S. Application Data which is a continuation-in-part of application No. 18/218,503, filed on Jul. 5, 2023, now Pat. No. 12,140,748, which is a continuation of application No. 17/744,711, filed on May 15, 2022, now Pat. No. 11,740,449, which is a continuation of application No. 17/527,130, filed on Nov. 15, 2021, now Pat. No. 11,359,798, which is a continuation of application No. 17/233,467, filed on Apr. 17, 2021, now Pat. No. 11,231,165.

(60) Provisional application No. 63/631,327, filed on Apr. 8, 2024, provisional application No. 63/013,487, filed on Apr. 21, 2020.

(51) Int. Cl.

| | |
|---|---|
| *A61B 90/30* | (2016.01) |
| *A61B 90/35* | (2016.01) |
| *A61B 90/50* | (2016.01) |
| *F21V 5/00* | (2018.01) |
| *F21V 5/04* | (2006.01) |
| *F21V 7/04* | (2006.01) |
| *F21V 11/08* | (2006.01) |
| *F21V 14/02* | (2006.01) |
| *F21V 19/02* | (2006.01) |
| *F21V 21/084* | (2006.01) |
| *F21V 23/00* | (2015.01) |
| *F21V 23/04* | (2006.01) |
| *F21Y 113/00* | (2016.01) |
| *F21Y 115/10* | (2016.01) |
| *G02B 5/20* | (2006.01) |
| *G02B 25/00* | (2006.01) |
| *G02C 7/08* | (2006.01) |

(52) U.S. Cl.
CPC ............ *A61B 5/7225* (2013.01); *A61B 90/30* (2016.02); *A61B 90/35* (2016.02); *A61B 90/50* (2016.02); *F21V 5/008* (2013.01); *F21V 5/04* (2013.01); *F21V 7/041* (2013.01); *F21V 11/08* (2013.01); *F21V 14/02* (2013.01); *F21V 19/02* (2013.01); *F21V 21/084* (2013.01); *F21V 23/003* (2013.01); *F21V 23/04* (2013.01); *G02B 5/208* (2013.01); *G02B 25/004* (2013.01); *G02B 25/008* (2013.01); *A61B 5/0071* (2013.01); *A61B 5/0088* (2013.01); *A61B 2090/309* (2016.02); *A61B 2090/502* (2016.02); *A61B 2560/0214* (2013.01); *F21Y 2113/30* (2023.05); *F21Y 2115/10* (2016.08); *G02C 7/086* (2013.01)

(58) Field of Classification Search
CPC . A61B 90/50; F21V 5/008; F21V 5/04; F21V 7/041; F21V 11/08; F21V 14/02; F21V 19/02; F21V 21/084; F21V 23/003; F21V 23/04

See application file for complete search history.

(56) References Cited

U.S. PATENT DOCUMENTS

| | | | |
|---|---|---|---|
| 9,068,716 B2 | 6/2015 | Kang | |
| 10,247,384 B1 | 4/2019 | Feinbloom | |
| 10,823,905 B2 * | 11/2020 | Dau ..................... | G02B 6/0078 |
| 2004/0080938 A1 * | 4/2004 | Holman .................. | F21S 41/12 |
| | | | 362/245 |
| 2007/0097703 A1 | 5/2007 | Goldfain | |
| 2010/0309646 A1 | 12/2010 | Morikawa | |
| 2012/0002416 A1 | 1/2012 | Kong, II | |
| 2012/0218522 A1 | 8/2012 | Namikawa | |
| 2013/0201561 A1 * | 8/2013 | McCluney ............... | F21S 11/00 |
| | | | 359/597 |
| 2013/0279197 A1 * | 10/2013 | Holman ............... | G02B 6/0068 |
| | | | 362/613 |
| 2014/0078715 A1 * | 3/2014 | Pickard .................... | F21K 9/62 |
| | | | 362/231 |
| 2014/0204580 A1 | 7/2014 | Yee | |
| 2014/0293582 A1 | 10/2014 | Lee | |
| 2014/0334159 A1 | 11/2014 | Ferguson | |
| 2015/0369469 A1 * | 12/2015 | Vamberi ................. | E01F 9/559 |
| | | | 362/267 |
| 2021/0396988 A1 | 12/2021 | Steier | |
| 2022/0074577 A1 | 3/2022 | Feinbloom | |
| 2023/0359015 A1 | 11/2023 | Feinbloom | |
| 2024/0369855 A1 | 11/2024 | Feinbloom | |

FOREIGN PATENT DOCUMENTS

| | | |
|---|---|---|
| KR | 1020070090542 | 11/2009 |
| WO | WO 2009/138228 | 11/2009 |

OTHER PUBLICATIONS

Notification of Transmittal of the International Search Report and the Written Opinion of the International Searching Authority or the Declaration—Dated Jun. 12, 2025.

"Notification of Transmittal of International Search Report and the Written Opinion of the International Searching Authority or the Declaration," Sep. 18, 2024.

* cited by examiner

Convergence at 20 inches

| Lens power (diopters) | Angle | % convergence |
|---|---|---|
| 8.0 | 90 | 0 |
| 16.0 | 90 | 0 |
| 24.0 | 90 | 0 |
| 8.0 | 77 | approx. 80 |
| 16.0 | 77 | ------ |
| 24.0 | 77 | ------ |
| 8.0 | 75 | ------ |
| 16.0 | 75 | approx. 100 |
| 24.0 | 75 | ------ |
| 8.0 | 70 | ------ |
| 16.0 | 70 | ------ |
| 24.0 | 70 | approx. 90 |

FIG. 14E

Convergence at 16 inches

| Lens power (diopters) | Angle | % convergence |
|---|---|---|
| 8.0 | 90 | 0 |
| 16.0 | 90 | 0 |
| 24.0 | 90 | 0 |
| 8.0 | 77 | approx. 100 |
| 16.0 | 77 | ------ |
| 24.0 | 77 | ------ |
| 8.0 | 75 | ------ |
| 16.0 | 75 | approx. 90 |
| 24.0 | 75 | ------ |
| 8.0 | 70 | ------ |
| 16.0 | 70 | ------ |
| 24.0 | 70 | approx. 75 |

FIG. 14D

MULTIPLE LIGHT SOURCE CONFIGURATION

CLAIM OF PRIORITY

This application claims, pursuant to 35 USC 120 as a Continuation-in-part application priority to and the benefit of the earlier filing date of patent application Ser. No. 18/664,080, filed on May 14, 2024, which claimed pursuant to 35 USC 119, priority to, and the benefit of the earlier filing date of provisional patent application Ser. No. 63/631,327, filed on Apr. 8, 2024, and pursuant to 35 USC 120, as a Continuation-in-Part application, priority to and the benefit of, the earlier filing date of patent application Ser. No. 18/218,503, filed on Jul. 5, 2023, which claimed, pursuant to 35 USC 120, as a Continuation application, priority to, and the benefit of the earlier filing date of patent application Ser. No. 17/744,711, filed on May 15, 2022, which claimed, as a Continuation application, priority to and the benefit of the earlier filing date of patent application Ser. No. 17/527,130, filed on Nov. 15, 2022 (U.S. Pat. No. 11,359,798), which claimed, as a Continuation application, priority to, and the benefit of the earlier filing date of patent application Ser. No. 17/233,467, filed on Apr. 17, 2021, (U.S. Pat. No. 11,231,165), which claimed priority to and the benefit of the earlier filing date, pursuant to 35 USC 119, as a non-provisional application, of patent application Ser. No. 63/013,487, filed on Apr. 21, 2020, the contents of all of which are incorporated by reference, herein.

FIELD OF THE INVENTION

This application is related to the field of lighting and more particularly a system for providing uniform light distribution from a plurality of light sources.

RELATED APPLICATION

This application is related to the U.S. Pat. Nos. 7,682,042; 8,851,709; RE 46463; U.S. Pat. No. 9,791,138; 10,240,769; 10,247,384; 10,527,254, and U.S. patent application Ser. Nos. 16/693,212 and 17/233,543, the contents of all of which are incorporated by reference, herein.

BACKGROUND OF THE INVENTION

Lighting devices are typically used in dental, medical and/or surgical fields to allow practitioners (e.g., dentist, doctor, surgeons, etc.) to apply light directly to the area where the practitioner is viewing. Some lighting devices may be free-standing lamps that a practitioner may position about the work area. Other lighting devices may be overhead lighting devices that operate on an arm that the practitioner may position about the work area. User-wearable (e.g., head-mounted) lighting devices may also be used by a practitioner to provide a tight light beam directly coincident with the practitioner's line of sight. Head-mounted lighting devices are advantageous as the projected light is directly at the focus of the practitioner's eyes and the practitioner's shadow is not projected onto the work area as in the case of overhead lights.

Operation of such head-mounted devices is known in the art. For example, U.S. Pat. No. 8,851,709; RE46463; U.S. Pat. Nos. 9,791,138; 10,240,769; and 10,527,254, which are assigned to the Assignee of the instant application, disclose user-wearable (e.g., head mounted) devices and their operation. Similarly, U.S. Pat. No. 7,682,042, which is assigned to the Assignee of the instant application, discloses an overhead or lamp configuration. The contents of all of which are incorporated by reference, herein.

Typically, with a head mounted lighting device, a practitioner (e.g., a dentist, a doctor, a surgeon) adjusts the lighting element such that the light is projected onto a surface to which the practitioner's eyes are focused. The practitioner may then control the light output in a manner as disclosed in the aforementioned US patents.

In addition to projecting a light (such as a white light) for assisting the practitioner in viewing the targeted area, the light source may be composed of different lighting sources that may be used for different purposes. For example, the light sources may generate an ultra-violet light (non-visible wavelength range), a visible light (e.g., white, red, green, blue, etc.) or an Infra-red (IR) (non-visible wavelength), wherein the specific wavelength band may achieve a desired purpose. For example, some light wavelengths are known to decrease the time of gel-like materials to harden. In addition, the lighting devices may comprise one or more of the different light sources may be generating a corresponding light concurrently; the control of which may require wired or wireless control circuitry.

However, user-wearable devices are required to be compact and lightweight, which limits the number light emitting elements that may be used in emitting a light. The limited number of lighting emitting elements limits the overall intensity of the light output by the head-mounted lighting device.

Hence, there is a need in the industry for a system that allows for a greater emission distribution of light from lighting devices; particularly of the user-wearable kind.

SUMMARY OF THE INVENTION

In accordance with the principles of the invention, there is disclosed a lighting device for the generation of light from multiple lighting sources that provides a greater emission of the light from lighting devices.

In accordance with the principles of the invention, there is disclosed a lighting device comprising a plurality of lighting sources, wherein each of the lighting sources is configurable to provide light to a desired point or region.

In accordance with the principles of the invention, there is disclosed a lighting device comprising a plurality of lighting sources, where in the lighting sources may be individually controlled while the light output by each of the lighting sources may be directed to a desired point or region.

In accordance with the principles of the invention, there is disclosed a lighting device comprising a plurality of lighting sources, wherein the lighting sources may be controlled electronically and physically to direct a light to a desired point or region.

In accordance with the principles of the invention, there is disclosed a lighting system that allows for the mixing of light from a plurality of lighting sources, wherein the light is focused onto at a desired point or region.

In accordance with the principles of the invention, there is disclosed a lighting system comprising a plurality of lighting sources arranged concentrically about a central or optical axis of a lens system wherein the lighting sources are oriented with respect to the central axis such that the light emitted by the light sources targets the lens system at a point or region where the lens system projects the light to a desired focal point.

In accordance with the principles of the invention, there is disclosed a lighting system comprising a plurality of lighting sources arranged substantially perpendicular to a central or optical axis of a lens system, wherein the light emitted by the lighting sources targets a light director that re-directs the emitted light to the lens system at a point or region where the lens system projects the light to a desired focal point.

In accordance with the principles of the invention, there is disclosed a lighting device comprising a plurality of lighting sources arranged substantially skewed from an axis perpendicular to a central axis of a lens system, wherein the light emitted by the lighting sources targets a light director that re-directs the emitted light to the lens system at a point or region where the lens system projects the light to a desired focal point.

In accordance with the principles of the invention, there is disclosed a lighting system comprising a plurality of lighting sources that are arranged to emit light individually, concurrently or sequentially in one of more light wavelength bands toward a light director, which redirects the light to a lens system that projects the light to a desired focal point.

BRIEF DESCRIPTION OF THE DRAWINGS

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented in the cause of providing what is believed to be the most useful and readily understood description of the principles and conceptual aspects of the invention. In this regard, no attempt is made to show structural details of the invention, or in a scale, in more detail than is necessary for a fundamental understanding of the invention, the description taken with the drawings making apparent to those skilled in the art how the several forms of the invention may be embodied in practice. In the accompanying drawings.

It is to be understood that the figures and descriptions of the present invention described herein have been simplified to illustrate the elements that are relevant for a clear understanding of the present invention, while eliminating, for purposes of clarity, many other elements. However, because these omitted elements are well-known in the art, and because they do not facilitate a better understanding of the present invention, a discussion of such elements is not provided herein. The disclosure, herein, is directed also to variations and modifications known to those skilled in the art.

DETAILED DESCRIPTION OF THE INVENTION

Figure 1A:
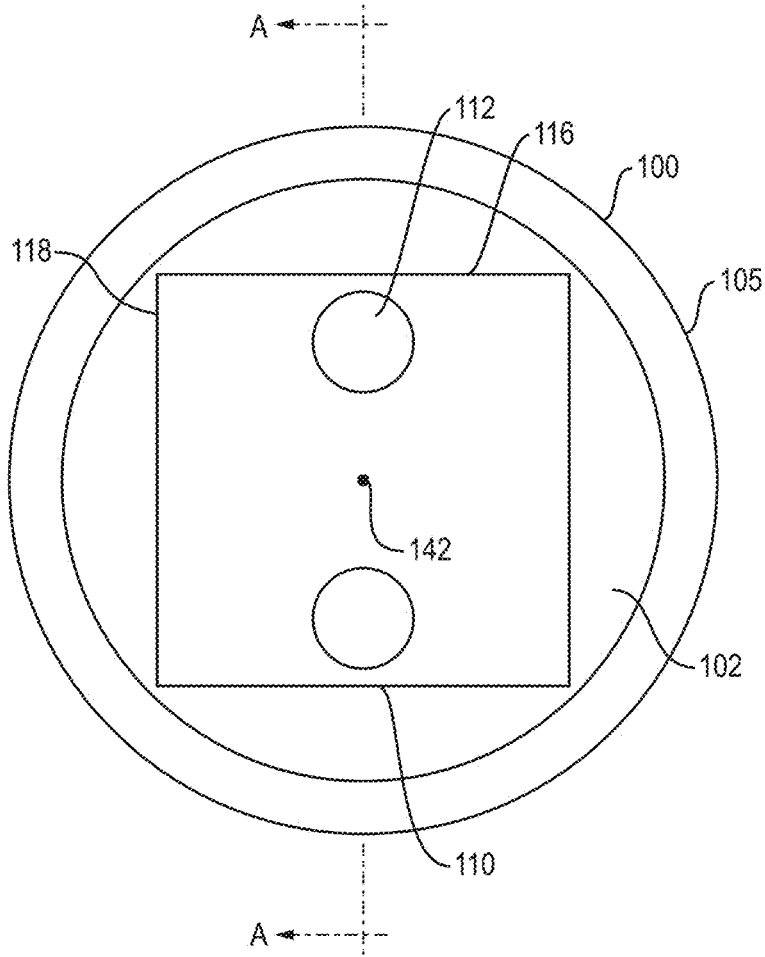
FIG. 1A illustrates a front view of a first exemplary embodiment of a lighting device comprising multiple light sources in accordance with the principles of the invention.

FIG. 1A illustrates a front view of a first exemplary embodiment of a lighting device comprising multiple light sources or elements in accordance with the principles of the invention.

In this illustrated front view, lighting device 100 comprises a housing 105 and a lens 102 through which lighting assembly 118 is visible. Lens 102 closes a distal end of lighting device 100.

Further illustrated are lighting sources 110 and 112 incorporated onto lighting assembly 118, wherein lighting sources s 110, 112 are positioned concentrically around or about a central or optical axis 142, which is formed by lens 102.

Lighting sources 110 and 112 are oriented with respect to the central or optical axis 142, which is positioned perpendicular to the plane of the page upon which the drawing is shown, to direct the light output by the plurality of lighting modules to a point (not shown).

Light emitted by lighting sources 110, 112 may be one of a white light (i.e., visible), a non-visible (i.e., an ultra-violet light, an infra-red light) or a visible light in one or more visible, non-white, light bands (referred to as colored light). More specifically, lighting sources 110, 112 may emit light in a non-visible ultra-violet wavelength range of about 10 to about 400 nanometer (nm). Or may emit light in one or more of a visible color light range. For example, in one or more specific color wavelength ranges (e.g., violet-380-435 nm; blue-435-495 nm; cyan-495-515; green-720-570 nm; yellow-570-590 nm; orange-590-620 nm and red-620-50 nm). Alternatively, lighting sources 110, 112 may emit a light in a non-visible infra-red wavelength range (greater than 700 nm). Additionally, lighting sources 110, 112 may emit light as a white light (i.e., 380-750 nm). Alternatively, lighting sources 110, 112 may emit light in or combinations of the discussed wavelength ranges.

Lighting assembly 118 further includes control unit 116 that controls the operation of the lighting sources 110, 112 to emit light. Control unit 116 may comprise one or more of resistors, transistors, diodes, capacitors that form dedicated hardware configuration and/or specialized hardware (e.g., ASIC, microcontroller, microprocessor) that enable control unit 116 to control the application of electrical energy to one or more of lighting sources 110, 112, etc.

Figure 1B:
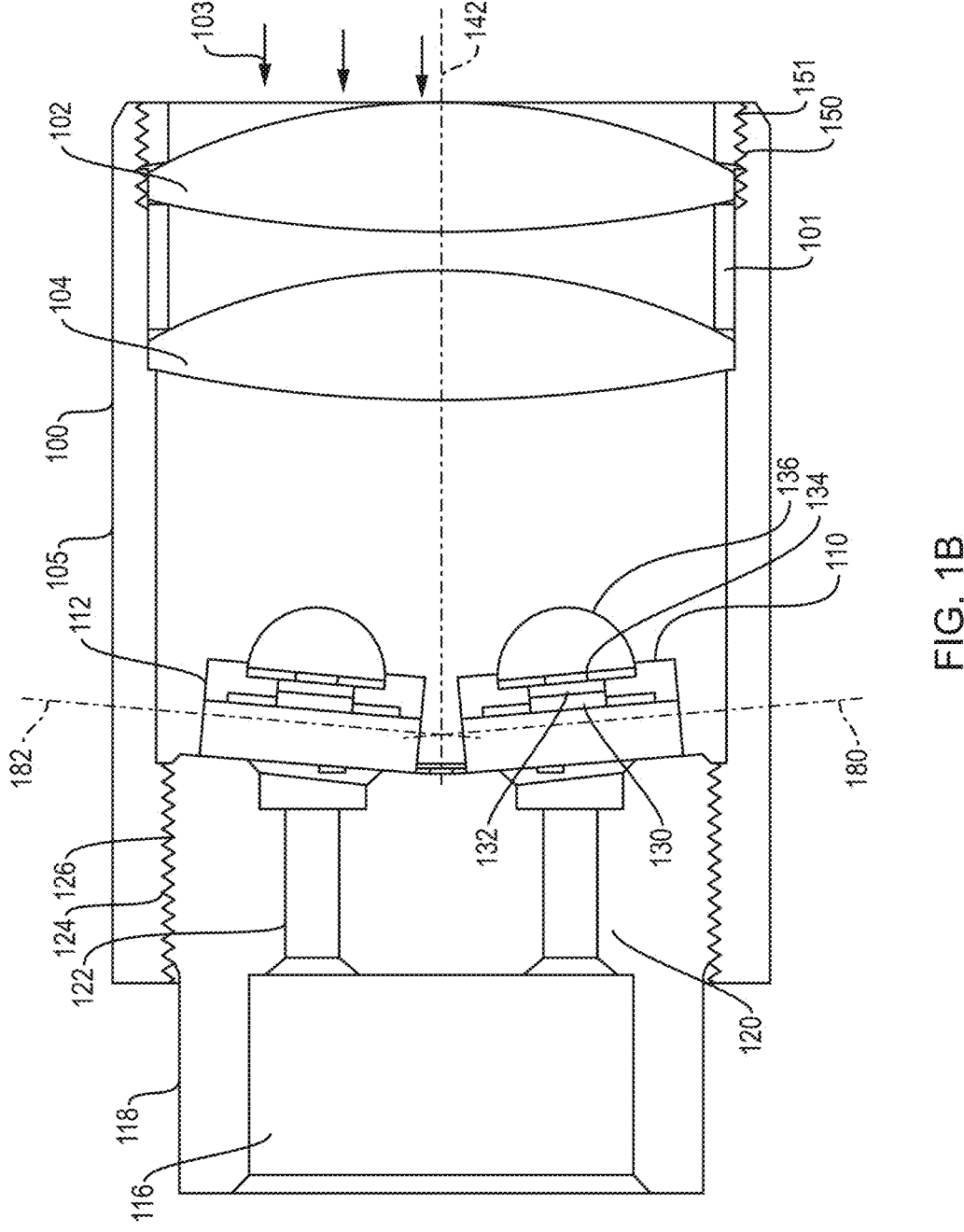
FIG. 1B illustrates a side view, through section A-A, of the first exemplary embodiment of the lighting device shown in FIG. 1A.

FIG. 1B illustrates a side view, through section A-A, of the first exemplary embodiment of the lighting device shown in FIG. 1A.

In this illustrated embodiment, lighting device 100 comprises lighting housing 105 into which lens assembly 101, comprising at least one objective lens 102, 104, is positioned at a first end of lighting housing 105. The at least one objective lens 102, 104 are substantially concentric and define a central or optical axis 142 of lighting device 100. The characteristics of lens 102, 104 form a focal point 250 onto which light 103 passing through lens assembly 101 converges.

Positioned at a second end of lighting housing 105 is lighting (or optical) assembly 118, which comprises control unit 116 and lighting sources 110 and 112. Connection between control unit 116 and lighting sources 110, 112 is provided by arms or extensions 120, 122. Arms 120, 122 provide a means for providing electrical energy to lighting sources 110, 112 and further providing for adjustment of lighting sources 110, 112 to change an angle of orientation of lighting source 110, 112 with respect of central or optical axis 142.

As is further shown, lighting assembly 118 and lens housing 101 may be mountable within light device 100 by a screw-thread connection (i.e., 124/126 150/151, respectively). Although a screw-thread connection is shown, it would be understood that other connections methods may be employed without altering the scope of the invention. For example, a snap-fit or a bayonet connection may be utilized for lighting assembly 118 and/or lens assembly 101.

In accordance with one aspect of the invention, lighting sources 110, 112 comprise holder 130, electronic section (i.e., printed circuit board) 132, light source 134 and lens 136. Holder 130 provides a means for retaining lighting sources 110 (112) within lighting assembly 118. Electronic section 132 comprising a printed circuit board, including known components, such as resistors, transistors, capacitors, special hardware circuitry (e.g., ASIC), and/or microcontroller/microprocessor, which control a flow of electrical energy (voltage/current) to light emitting sources 134. Light emitting sources 134 may comprise light emitting diodes (LEDs) that may possess lasing capability (i.e., semiconductor laser) or non-lasing capability (e.g., super-luminance diodes, etc.). Lens 136 provides for a concentration of the light emitted by light element or light emitting source 134.

A more detailed understanding of a preferred construction of lighting sources 110, 112 may be found in the referred to related US Patents wherein lighting sources 110 comprises at least one of: a light emitting source 134 (e.g., a light emitting diode), an aperture holder, an aperture and a dome lens, wherein the aperture holder and aperture are configured to adapt or configure the light outputted by the light element 134 and the dome lens 136 configured to concentrate the light outputted through the aperture.

For example, in the case of the emission of a white light, light element 134 may comprise a phosphor layer and a blue die positioned on the phosphor layer wherein the light emitted by light element 134 is primarily a white light. Aperture holder (not shown) may include a passthrough which is sized to allow the blue die element of light element 134 to passthrough, while blocking light emitted by the phosphor layer. An aperture, positioned on or within the aperture holder, may include a passthrough that may be sized to further reduce (adapt or configure) the amount of stray light of the phosphor layer to passthrough the aperture. In one aspect of the invention, the aperture passthrough may be sized to allow the blue die element of the light element 134 to passthrough. In another aspect of the invention, the aperture passthrough may be sized to allow only a center region of the blue die element of light element 134 to be viewable through the aperture passthrough and prevent the blue die element from being positioned within the aperture passthrough. In one aspect of the invention, the aperture holder passthrough may be substantially square or circular to allow the blue die element to passthrough, while the aperture passthrough may be circular or square and smaller than the blue die element. In addition, in accordance with the principles of the teachings of the related US patents, the light element 134 may be within a focal length of the dome lens 136.

Although a specific configuration of lighting sources 110, 112 is disclosed, it would be recognized that lighting source 110, 112 may include only electronic section 132 and light element 134, wherein at least one of the aperture holder, the aperture and dome lens 136 may not be utilized.

Returning to FIG. 1B, arm 120 provides electrical and mechanical connection from control unit 116 to lighting source 110. For example, control unit 116 may provide electrical energy to lighting source or element 110 such that a light may be emitted by lighting source or element 110. In one aspect of the invention, a magnitude (i.e., a drive current) of the electrical energy provided to lighting source or element 110 may be adjusted such that the light output may transition from a low output light to a high output light or from a light ON condition to a light OFF condition.

Extension arm 120 may be adjustable in a manner that changes an orientation of lighting source or element 110 with respect to optical axis 142.

In this illustrated embodiment lighting source 110 is oriented with respect to an axis 182 wherein axis 182 is offset from an axis (not shown) that is substantially perpendicular to optical axis 142.

In one aspect of the invention, arm 120 may comprise a screw thread (not shown), which when turned in a first (e.g., clockwise) direction may decrease the angle of axis 180 with respect to optical axis 142. Whereas, when turned in a second (e.g., counterclockwise direction), the angle of axis 180 with respect to optical axis 142 may increase.

Alternatively, offset axis 180 may be preset in a manner to satisfy the angle characteristics presented herein, wherein a light emitted by lighting source 110 converges to a point a known distance from lens 102.

Further illustrated is second lighting source 112 positioned opposite optical axis 142. Second lighting source 112 is similar in construction and electrical and physical operation to first lighting source 110 and a detailed discussion of the construction and operation of second lighting source 112 is not believed necessary, as those skilled in the art would understand both the construction and operation of second lighting source 112 from the discussion associated with lighting source 110.

Control unit 116 may further provide electrical energy to one or more of lighting sources 110, 112 in a manner such that the light emitted by lighting sources 110, 112 may be emitted concurrently, individually or sequentially.

Although controller 116 is shown as an individual element, it would be understood that the control function of controller 116 may be incorporated into the electronic components associated with PCB 132.

Hence, the illustrated element 116 may merely comprise a base onto which arms 120, 122 are positioned, and the control function may be included in PCB 132.

Accordingly, the lighting sources 110 and 112 may be referred to as lighting module 110/116 and 112/116 to illustrate the distributive nature of the electronic components associated with controller 116 and PCB 132.

Figure 2:
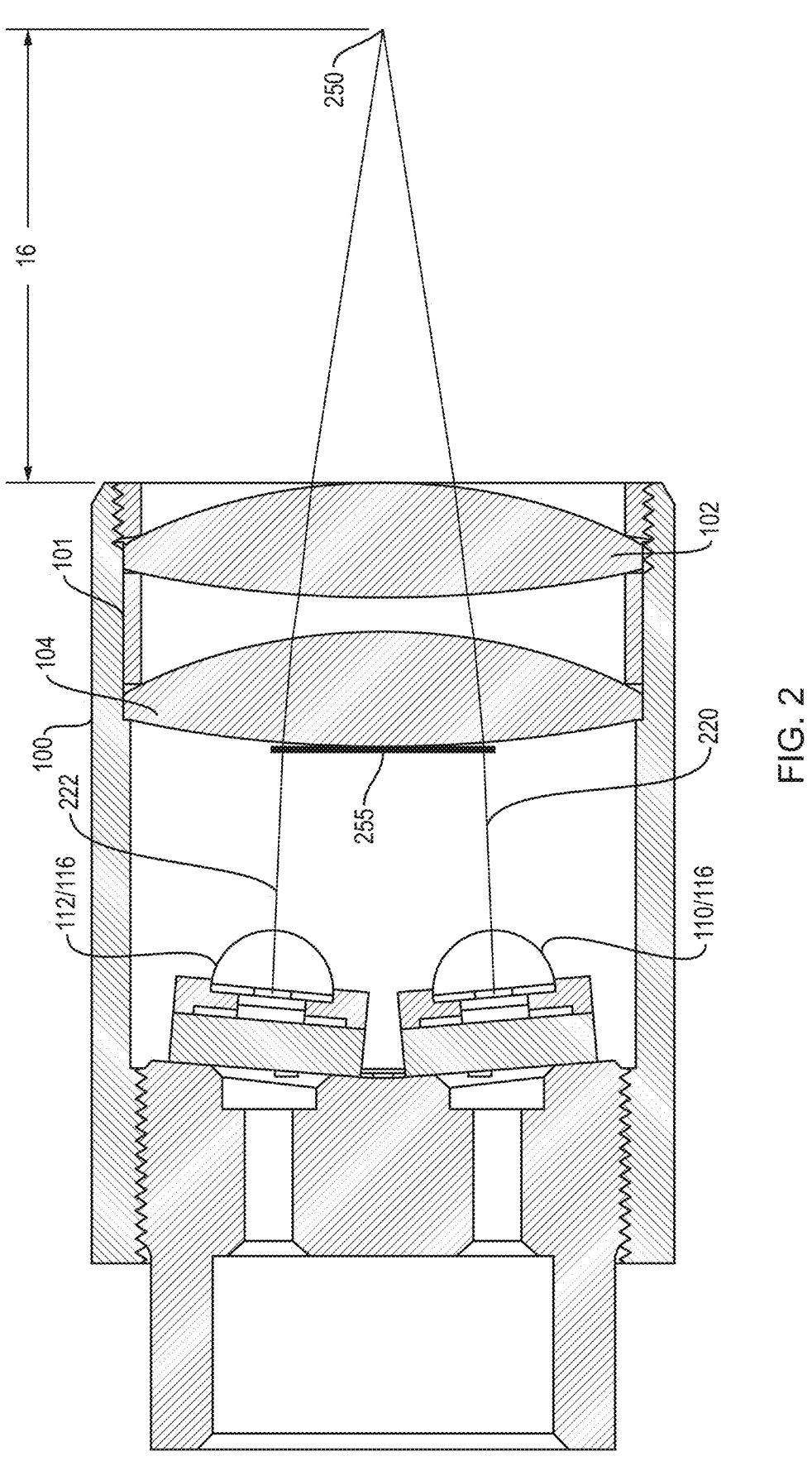
FIG. 2 illustrates a second side view, through section A-A, of the first exemplary embodiment of the lighting device shown in FIG. 1A.

FIG. 2 illustrates a second side view, through section A-A, of the first exemplary embodiment of the lighting device shown in FIG. 1A.

In this illustrated aspect of the invention of lighting device 100, first lighting module 110/116 generates light directed along light path 220 toward a region 255 on lens assembly 101. Similarly, second lighting module 112/116 generates light directed toward a region 255 on lens assembly 101 along light path 222.

The light generated by first lighting module 110/116 and second lighting module 112/116 passes through lenses 104 and 102 of lens assembly 101, wherein the optical characteristics of lenses 102, 104 are selected to direct the light toward point 250 (i.e., area about point 250). In this case, known point 250 is illustrated to be approximately 16 inches from lighting device 100.

Although sixteen (16) inches is illustrated as the point of convergence 250 of the light emitted by lighting device 100, it would be understood that the use of the measurement of 16 inches is only to illustrate the convergence of the light and other distances or measurements from lighting device 100 may be achieved by changing the relationship between lighting modules 110/116, 112/116 and lens housing 101. Hence, other distances (or focal points) are considered within the scope of the invention claimed.

Figure 3:
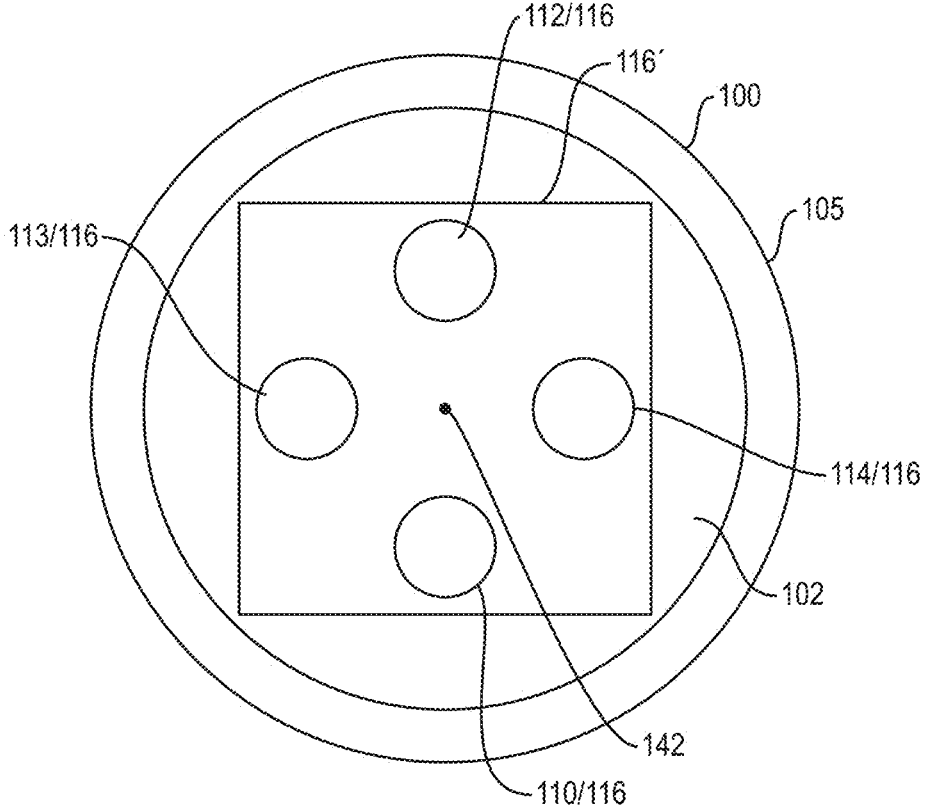
FIG. 3 illustrates a front view of a second aspect of the first exemplary embodiment shown in FIGS. 1A, 1B and 1C.

FIG. 3 illustrates a front view of a second aspect of the first exemplary embodiment shown in FIGS. 1A, 1B and 1C.

In this illustrated front view, a plurality of lighting modules (e.g., first lighting module 110/116, second lighting module 112/116, third lighting module 113/116 and fourth lighting module 114/116) are positioned concentrically around optical axis 142, wherein each of the plurality of lighting modules is attached to corresponding extensions (not shown), which are attached to base 116'. Electrically energy (voltage, current) may be applied to the lighting modules 110/116 . . . 114/116, through extensions (not shown) as previously discussed, wherein the electronic elements of controller 116/PCB 132 control the application of the voltage to corresponding lighting modules.

The plurality of lighting modules 110/116 . . . 114/116 are oriented, as discussed, to direct the light outputted by the plurality of lighting modules to a focus point 250 (not shown).

Although four (4) lighting modules are illustrated, it would be recognized that the number of lighting modules may be increased (i.e., greater than the illustrated 4) or decreased (i.e., 2 or 3) without altering the scope of the invention.

Figure 4A:
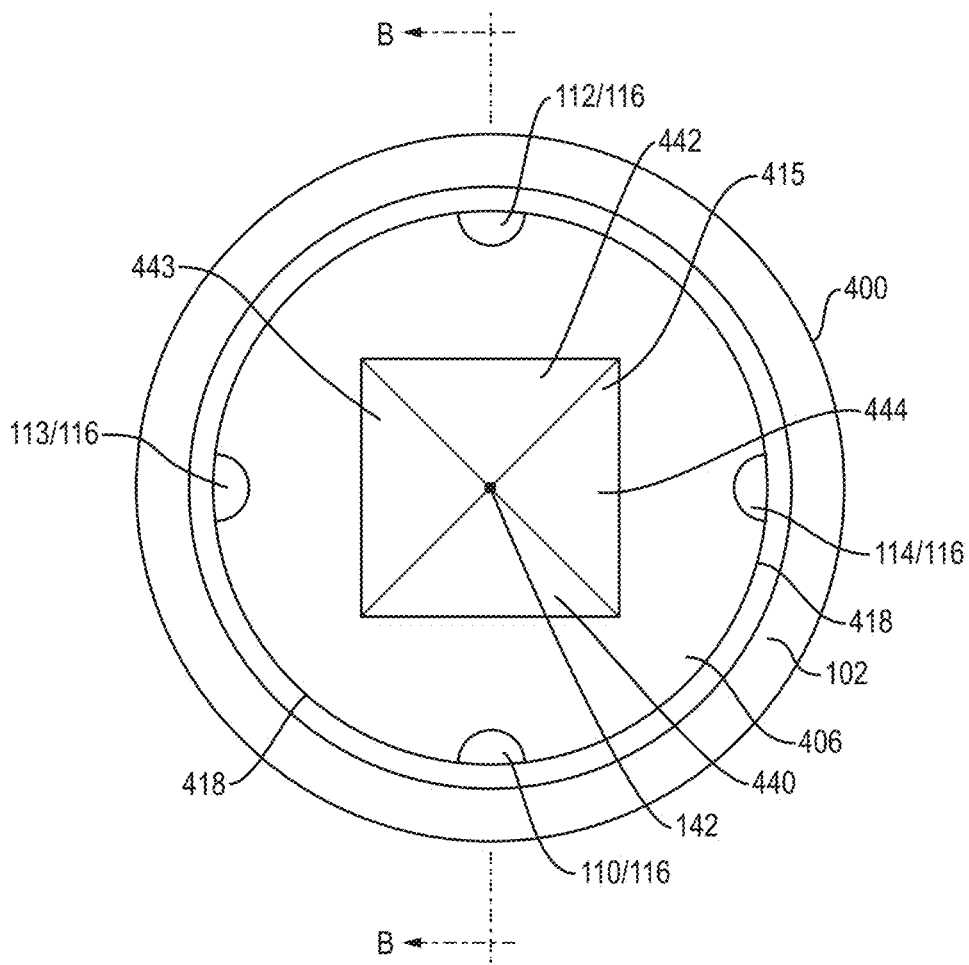
FIG. 4A illustrates a front view of a first aspect of a second exemplary embodiment of a lighting device 400 in accordance with the principles of the invention.

FIG. 4A illustrates a front view of a first aspect of a second exemplary embodiment of a lighting device 400 in accordance with the principles of the invention.

In this illustrated front view of lighting device 400, a plurality of lighting sources and associated distributed controllers (referred to as first lighting module 110/116, second lighting module 112/116, third lighting module 113/116 and fourth lighting module 114/116) are shown positioned along an inner circumference surface of lighting assembly 418. Further illustrated is light director 415 extending from base 406 of lighting assembly 418, wherein light director 415 is in a shape of a 4-sided pyramid (i.e., prismatic structure). In addition, each of the sides or lateral faces of the illustrated light director 415 may include a reflective surface (e.g., aluminum, mirror, etc.) 440, 442, 444, 446, that redirects light emitted by one or more of the lighting modules toward lens assembly 101.

In accordance with the principles of the invention, light emitted by lighting modules 110/116, 112/116, 113/116, 114/116 is directed to a corresponding one of the lateral faces (which include reflective surfaces) such that the emitted light, which is in the plane of the paper the drawing is shown on, is redirected such that the emitted light is directed perpendicular to the plane of the paper the drawing is shown on. In accordance with the principles of the invention the light emitted by lighting modules 110/116 . . . 114/116 may be emitted individually, concurrently or sequentially.

Figure 4B:
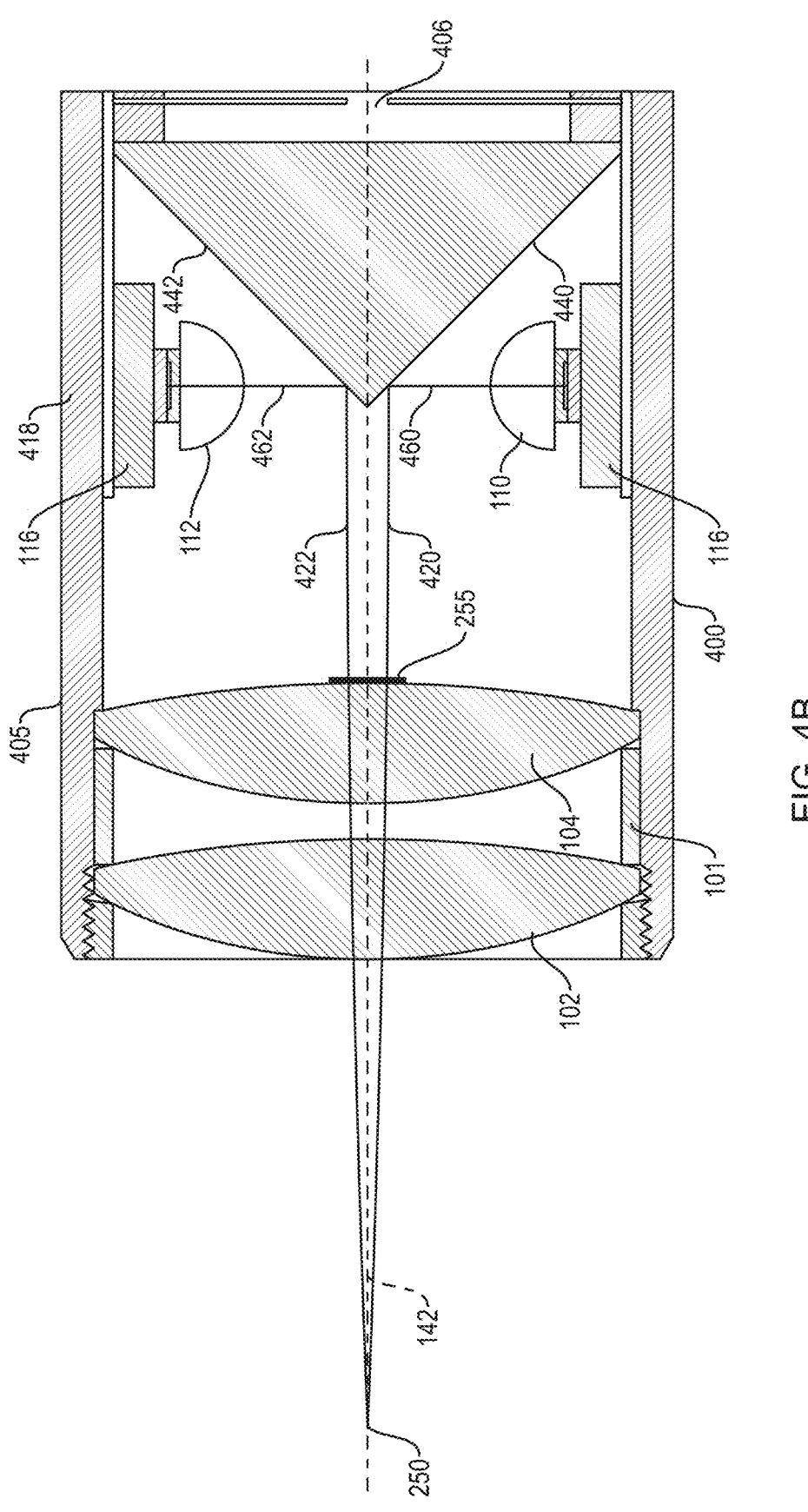
FIG. 4B illustrates a side view, through section B-B, of the first aspect of the second exemplary embodiment of a lighting device shown in FIG. 4A.

FIG. 4B illustrates a side view, through section B-B, of the first aspect of the second exemplary embodiment of the lighting device shown in FIG. 4A.

In this second exemplary embodiment, lighting device 400 comprises a lighting housing 405 comprising lens assembly 101 positioned on a first end of lighting housing 405 and lighting assembly 418 positioned on a second, opposing end of light housing 405. Lens assembly 101 comprises at least one objective lens 102, 104 forming an optical axis 142 on which focal point 250 is formed, as previously discussed.

Further illustrated is lighting assembly 418 comprising a first lighting module 110/116 (as first lighting source 110 and associated controller 116) and second lighting module (second lighting source 112 and associated controllers 116) positioned around or about an inner circumference to lighting assembly 418. The illustrated first lighting source 110 and second lighting source 112 are similar in construction to lighting source 110, 112 shown in, and described, with regard to FIGS. 1A, 1B and 2. Although only two lighting modules are shown, it would be recognized that a greater number of lighting modules may be distributed about the inner surface of lighting assembly 418.

Furthermore, although lighting assembly 418 is shown without a screw thread attachment to housing 405, it would be understood that lighting assembly 418 may be removably attached to lighting housing 405 through at least one of: a screw thread, a snap-fit, a bayonet, etc., type connection in a manner similar to that discussed with regard to lighting assembly 118 shown in FIG. 1B, for example. Alternatively, lighting assembly 418 may be integrated into lighting housing 405.

In this first aspect of the second exemplary embodiment of a multi-light source lighting device, first lighting module 110/116 and second lighting module 112/116, positioned along an internal circumference of lighting assembly 418, emit or generate a light that is substantially perpendicular to optical axis 142 along light path 460, 462, respectively.

Light director 415 operates to receive the light emitted by lighting modules 110/116, 112/116 and redirect the emitted light toward region 255 on lens assembly 101, along light paths 420, 422, respectively, wherein the optical characteristics of lenses 102, 104 are selected to direct the light toward point 250 (i.e., area about point 250).

In this illustrated embodiment, light director 415 comprises a pyramid shaped element positioned on base 406, wherein the sides or lateral faces of light director 415 extend from base 406 at an angle oriented at substantially a forty-five (45) degree angle with respect to optical axis 142 and forming a ninety (90) degree or right angle at an apex of light director 415, to allow light generated or emitted by first lighting module 110/116 and second lighting module 112/116 to be redirected toward region 255 on lens assembly 101.

Light director 415 further comprises reflective surfaces 440, 442, on at least a portion of corresponding one of its lateral surfaces, wherein reflective surfaces 440, 442 operate to redirect a substantial portion of the light generated or emitted by first lighting module 110/116 and second lighting module 112/116 toward lens assembly 101.

In accordance with the principles of the invention, light directed along light paths 420 and 422 is outputted by lens assembly 101 such that the optical properties of lenses 102, 104 within lens assembly 101 converges the light onto known point 250, as previously discussed.

Although, lighting modules 110/116 and 112/116 are shown in a distributed controller configuration, it would be recognized that the controller 116 may be remote from lighting sources 110, 112, as shown in FIG. 1B, for example, without altering the scope of the invention claimed.

Figure 4C:
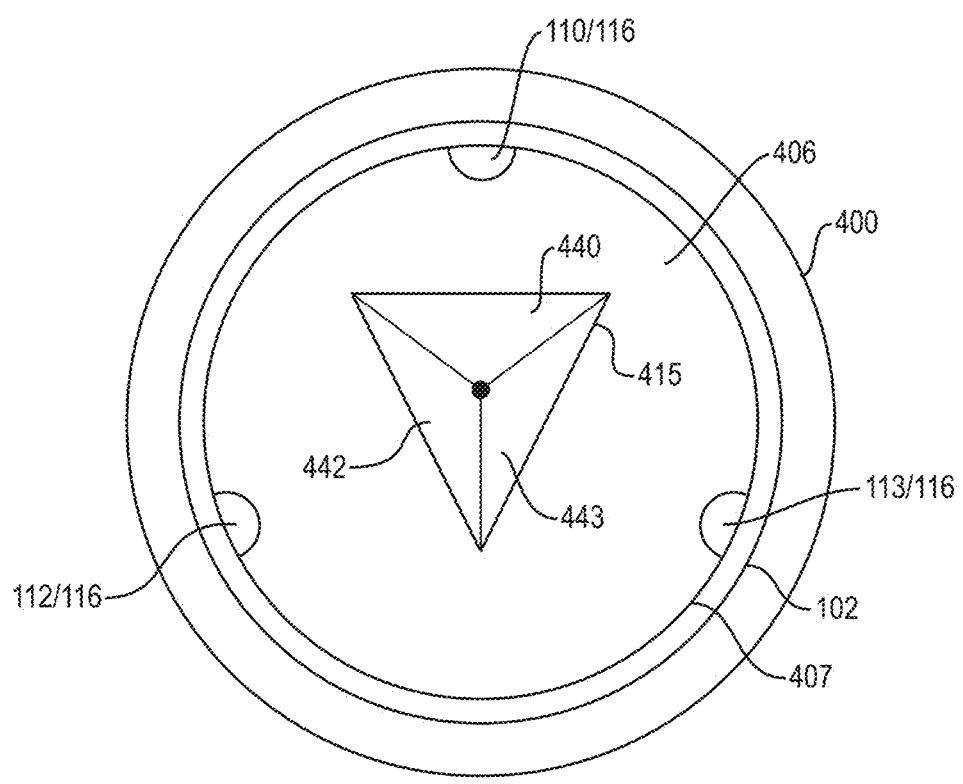
FIG. 4C illustrates a front view of a second aspect of the second exemplary embodiment of a lighting device shown in FIG. 4A.

FIG. 4C illustrates a front view of a second aspect of the second exemplary embodiment of a lighting device shown in FIG. 4A.

In this illustrated front view, a plurality of lighting modules (e.g., first lighting module 110/116, second lighting module 112/116, and third lighting module 113/116) are shown positioned along an inner circumference surface of lighting assembly 418. Further illustrated is light director 415 extending from base 406 of lighting assembly 418, wherein light director 415 is in a shape of a tetrahedron (i.e., a 3-sided pyramid). In addition, each of the lateral surfaces (or portions thereof) of light director 415 may include a reflective surface 441, 442, 443, respectively, to reflect a substantial portion of the light emitted by corresponding ones of the lighting modules.

As previously discussed, the light emitted by the lighting modules 110/116, 112/116, 113/116, may be emitted concurrently, individually or sequentially and directed toward region 255 on lens assembly 101.

Although light director 415 shown in FIG. 4A is shown as a 4-sided pyramid and shown in FIG. 4C as a 3-sided pyramid, it would be recognized that a number of sides or lateral faces of light director 415 may be increased or decreased without altering the scope of the invention. For example, the number of lateral faces of the light director 415 may be determined based on a number of lighting modules positioned along the inner circumference surface of lighting assembly 418. Alternatively, light director 415 may include an infinite number of sides (i.e., a cone or conical shape), which is independent of the number of lighting modules.

Figure 5A:
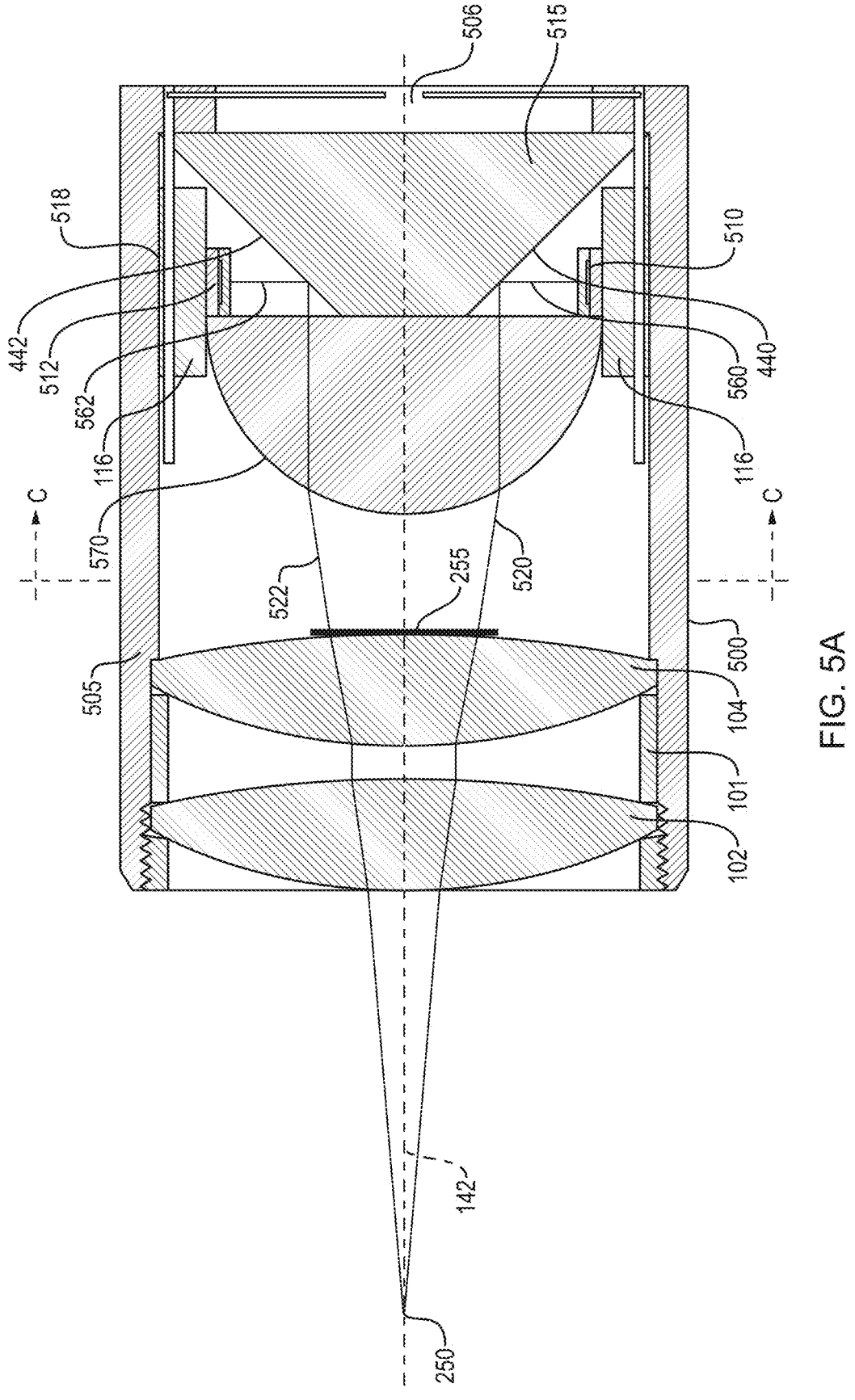
FIG. 5A illustrates a side view of a first aspect of a third exemplary embodiment of a lighting device comprising multiple light sources in accordance with the principles of the invention.

FIG. 5A illustrates a side view of a first aspect of a third exemplary embodiment of a lighting device comprising multiple light sources in accordance with the principles of the invention.

In this third exemplary embodiment, light device 500 comprises a housing 505 and lens assembly 101 comprising at least one lens 102, 104 forming an optical axis 142 onto which is formed focal point 250.

Further illustrated is lighting assembly 518 positioned at a second end of housing 506. Lighting assembly 518 comprises first lighting module 510/116 (i.e., lighting source 510 and controller 116) and second lighting module 512/116 (i.e., lighting source 512 and controller 116) positioned along an inner circumference surface of lighting assembly 518 and a light director 515. In this illustrated embodiment, first lighting source 510 and second lighting source 512 are similar to light sources 110, 112, shown and described with regard to FIG. 1B. However, lighting sources 510 and 512 lack one or more of the aperture holder, aperture, dome lens disclosed with regard to first lighting source 110 and second lighting source 112. In this specific illustrated embodiment, lighting sources 510, 512 lack dome lens 136.

In addition, lighting assembly 518 may, similar to lighting assembly 418, be removably attachable to housing 505 or integrated into housing 505.

Light director 515 is similar to light director 415, previously described. However, in this illustrated embodiment light director 515 is represented as a clipped pyramid or cone shaped element positioned on base 506. That is, the term "clipped pyramid or clipped cone" represents a geometrical pyramid (or cone) in which a top portion has been removed. When viewed as a 3-dimensional object, light director 515 is in the form of a 3-dimensional trapezoidal shaped object.

Light director 515, which is oriented at a substantially 45-degree angle with respect to optical axis 142, comprises reflective surfaces 440, 442 that operate to redirect light generated by first lighting module 510/116 and second lighting module 512/116, as discussed with regard to FIG. 4B.

Further illustrated is lens 570 positioned substantially perpendicular to optical axis 142. In this illustrated example, lens 570 is positioned in contact with light director 515 and is sized such that light redirected from reflective surfaces 440, 442 is captured by lens 570.

In accordance with this embodiment of the invention, light emitted by first lighting module 510/116 is directed along light path 560 and impinges upon reflective surface 440, which redirects the light along light path 520 toward lens 570. Similarly, light emitted by second lighting module 512/116 is directed along light path 562 and impinges upon reflective surface 442. Reflective surface 442 redirects the light along light path 522 toward lens 570.

Lens 570 concentrates the light directed along light paths 520, 522 toward region 255 on lens assembly 101, wherein the optical properties of lenses 102, 104 converges the light onto known point 250, as previously discussed.

Although lens 570 shown in FIG. 5A is depicted as extending a width of lighting assembly 518, it would be understood that lens 570 may be included within a holder that extends the width of lighting assembly 518, wherein the holder retains lens 570 in place and lens 570 may be sized to be sufficient to capture the light redirected by light director 515.

Figure 5B:
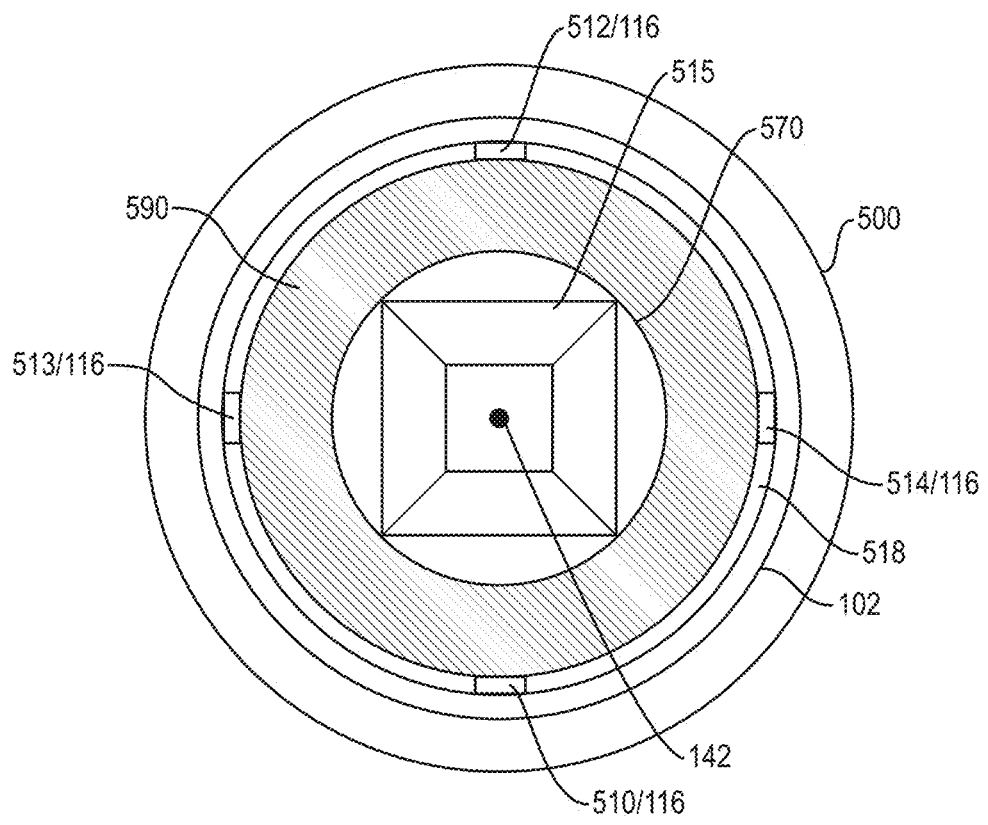
FIG. 5B illustrates a front view of a second aspect of the third exemplary embodiment shown in FIG. 5A.

FIG. 5B illustrates a front view of the second aspect of the third exemplary embodiment shown in FIG. 5A.

In this illustrated front view, a plurality of lighting modules (e.g., first lighting module 510/116, second lighting module 512/116, third lighting module 513/116 and fourth lighting module 514/116) are shown positioned along an inner circumference surface of lighting assembly 518. Further illustrated is light director 515 extending from base 506 of lighting assembly 518, wherein light director 515 is in a shape of a 4-sided clipped pyramid.

Further illustrated is lens 570 positioned substantially perpendicular to the optical axis 142 within holder 590. Holder 590 extends the width of lighting assembly 518 and retains lens 570 in place.

Figure 6:
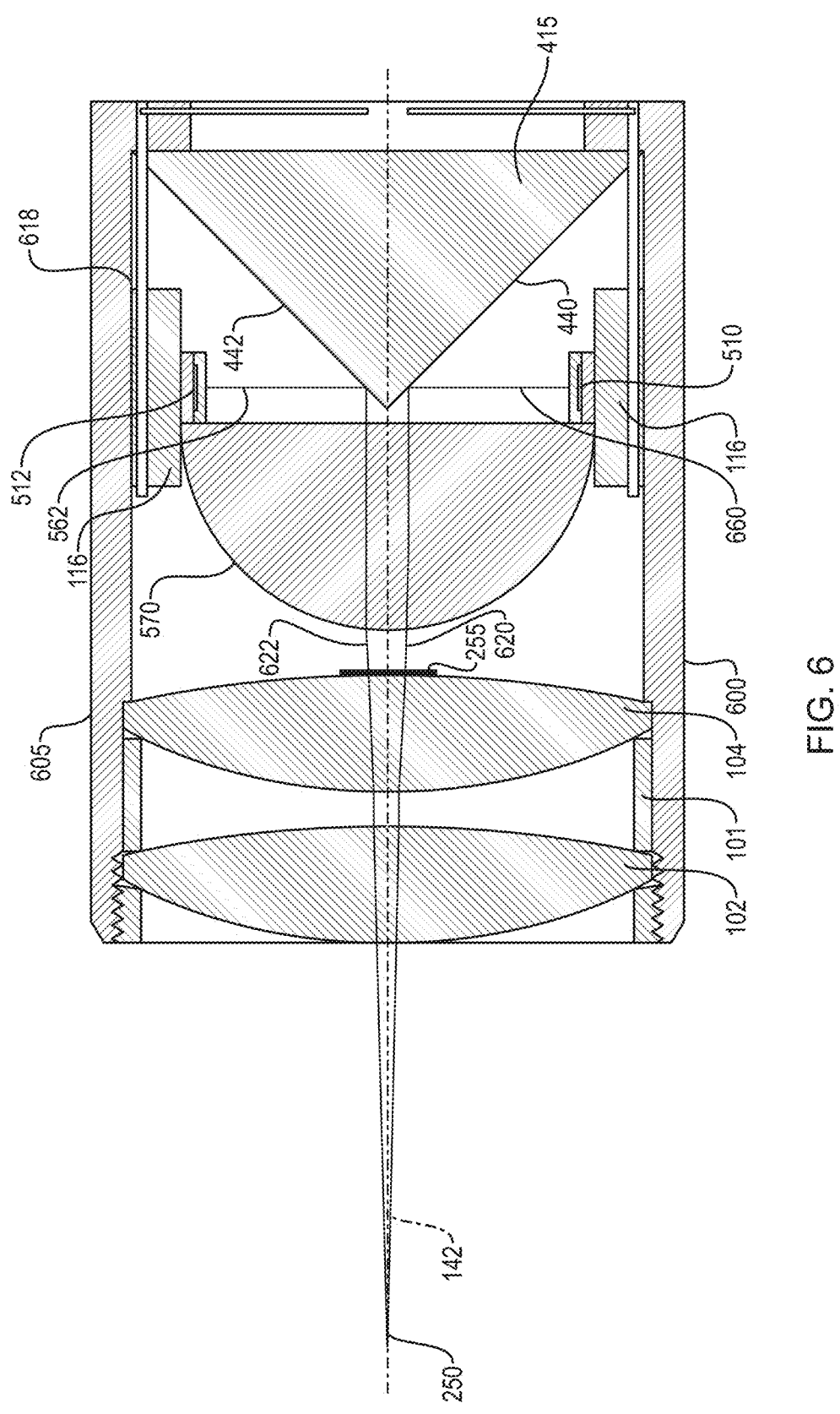
FIG. 6 illustrates a side view of a fourth exemplary embodiment of a lighting device comprising multiple light sources in accordance with the principles of the invention.

FIG. 6 illustrates a side view of a fourth exemplary embodiment of a lighting device comprising multiple light sources in accordance with the principles of the invention.

In this fourth exemplary embodiment, lighting device 600 comprises housing 605 and lens assembly 101 comprising at least one lens 102, 104 forming an optical axis 142.

Further illustrated is lighting assembly 618 comprising first lighting module 510/116 and second lighting module 512/116, positioned along an inner circumference surface of lighting assembly 618 and light director 415.

First lighting module 510/116 and second lighting module 512/116 are similar to those elements described with regard to FIG. 5A and light director 415 is similar to the light director 415 described with regard to FIGS. 4A, 4B.

Light director 415, whose sides or lateral surfaces are oriented at a substantially 45-degree angle with respect to optical axis 142 comprises reflective surfaces 440, 442, which operate to redirect light emitted by first lighting module 510/116 and second lighting module 512/116.

Further illustrated is lens 570 positioned substantially perpendicular to optical axis 142. Lens 570 is sized to capture light redirected from reflective surfaces 440, 442 and direct the capture light toward lens assembly 101.

In this illustrated example, light emitted by first lighting module 510/116, directed along light path 660 and impinges upon reflective surface 440, which redirects light toward lens 570 and lens assembly 101, along light path 620. Similarly, light emitted by second lighting module 512/116, directed along light path 562 impinges upon reflective surface 442, which directs light toward lens 570 and lens assembly 101 along light path 622.

In accordance with the principles of the invention, light directed along light paths 620 and 622 is output by lens assembly 101 such that the output light converges onto known point 250.

Although lens 570 shown in FIG. 6 is depicted as extending the width of optical assembly 618, it would be understood that lens 570 may be included within a holder that extends the optical assembly 618 in a manner similar to that shown in FIG. 5B.

Figure 7:
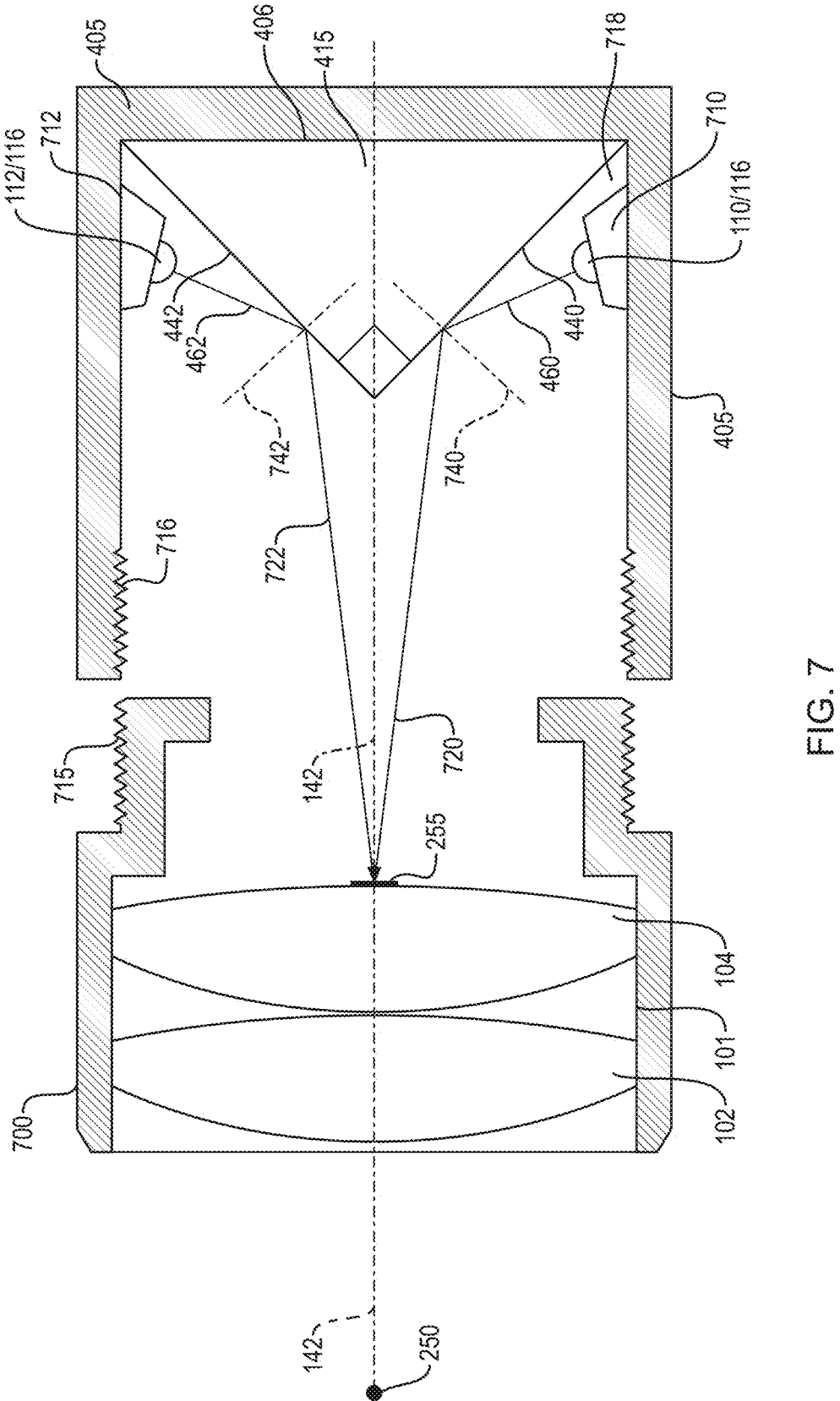
FIG. 7 illustrates a side view of a third aspect of the second exemplary embodiment of the lighting device shown in FIGS. 4A-4C.

FIG. 7 illustrates a side view of a third aspect of the second exemplary embodiment of the lighting device shown in FIGS. 4A-4B, wherein the lighting sources 110, 112 (or lighting modules 110/116, 112/116) are configured to cause light director 415 to redirect light to a known region 255 within lens assembly 101, a previously discussed.

In this illustrated embodiment, lighting device 700 comprises lighting housing 405 comprising lens housing 101, wherein lens housings 101 includes lenses 102 and 104, and lighting assembly 718 includes light director 415, as previously discussed.

In this illustrated embodiment, which is similar to the embodiments shown in FIGS. 4A, 4B, 4C, 5A, 5B, and 6, lens housing 101 may be removably attachable to lighting housing 405, through the illustrated screw thread 715/716. Although a screw thread connection is shown it would be recognized that lens housing 101 and lighting housing 405 may comprise other forms of connections as previously discussed. Similarly, lighting assembly 718 may be removably attachable to housing 405 as shown in FIGS. 1A, 1B, for example.

Further illustrated are reflective surfaces 440 and 442, which reflect light at an angle equal to the angle of the light incident to reflective surfaces 440, 442, with respect to an axis 740, 742 normal to reflective surface 440, 442, respectively.

In this third aspect of the embodiment shown in FIGS. 4A-4B, lighting sources 110 and 112 (or lighting modules 110/116, 112/116) are positioned along the interior surface of lighting housing 405 at an angle 710, 712 with respect to optical axis 142. Accordingly, the light emitted by lighting sources 110, 112 (or lighting modules 110/116, 112/116) is not perpendicular to, but skewed (or slanted) from optical axis 142.

The angle at which light sources 110, 112 (or lighting modules 110/116, 112/116) is offset from the optical axis 142 may be selected or determined to cause the light projected or emitted by lighting sources 110, 112 (or lighting modules 110/116, 112/116) along light paths 460, 462, respectively, to be reflected from reflective surfaces 440, 442 along paths 720, 722 so as to be directed to known region 255 on lens assembly 101.

Region 255 may be determined, in part, based on the characteristics of lens 102, 104 such that the light emitted by lighting sources 110, 112 (or lighting modules 110/116, 112/116) converges at known point 250, as discussed previously.

Figure 8A:
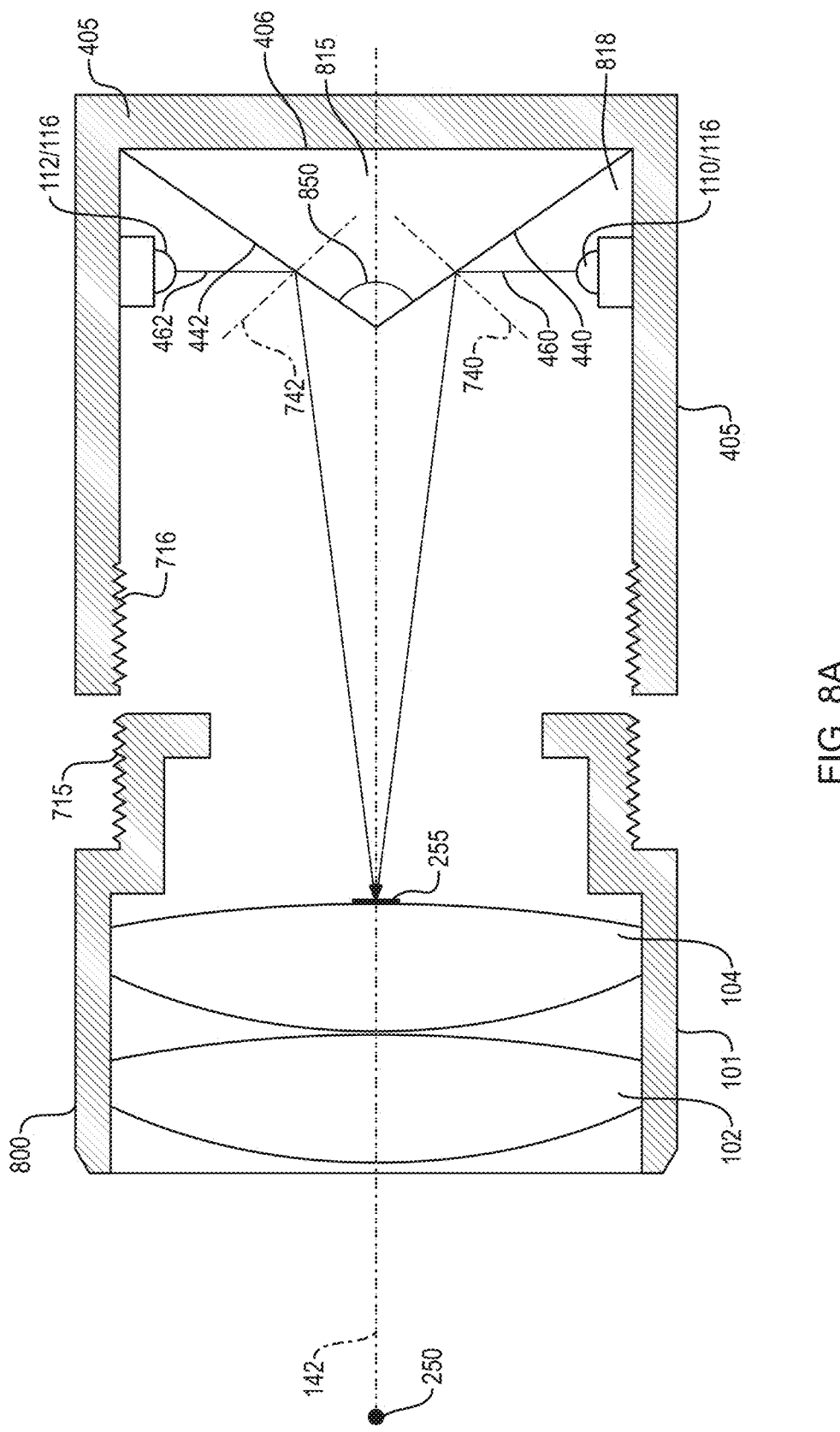
FIGS. 8A and 8B illustrate side views of a fourth and fifth, respectively, aspects of the second exemplary embodiment of the lighting device shown in in FIGS. 4A-4C.

FIG. 8A illustrates a side view of a fourth aspect of the second exemplary embodiment of the lighting device shown in in FIGS. 4A-4B.

In this illustrated aspect of the second embodiment shown in FIGS. 4A-4C, lighting device 800 comprises lighting housing 405 comprising lens housing 101, wherein lens housings 101 includes lenses 102 and 104, removably attachable to lighting housing 405, and lighting assembly 818, similar to the configuration shown in shown in FIGS. 4A, 4B, comprising lighting sources 110, 112 (or lighting modules 110/116, 112/116) positioned about an inner circumference of light assembly 818.

In accordance with the principles of operation of this illustrated embodiment, light sources 110 and 112 (or lighting modules 110/116, 112/116) are arranged along the interior surface of lighting housing 405 (or lighting assembly 818) such that light paths 460, 462 are substantially perpendicular to optical axis 142.

Further illustrated is light director 815, which is similar to light director 415, including reflective surfaces 440, 442, which reflects light projected onto reflective surfaces 440, 442, at an angle equal to the angle of the light incident to light director 815.

In this illustrated embodiment, the peak angle 850 of light director 815, as shown, is an obtuse angle (i.e., greater than 90 degrees) to enable the light emitted by lighting modules 110/116, 112/116, to be reflected toward lens assembly 101, wherein the optical characteristics of lenses 102, 104 are selected to direct the light toward point 250 (i.e., area about point 250).

As is known in the art, the light reflected by a reflective surface is reflected at an angle, with respect to a normal (i.e., axis 740, 742) that is equal to the angle of incidence of light, wherein reflected light, in a manner similar to that discussed with regard to FIG. 7, is directed along light paths 720, 722.

Figure 8B:
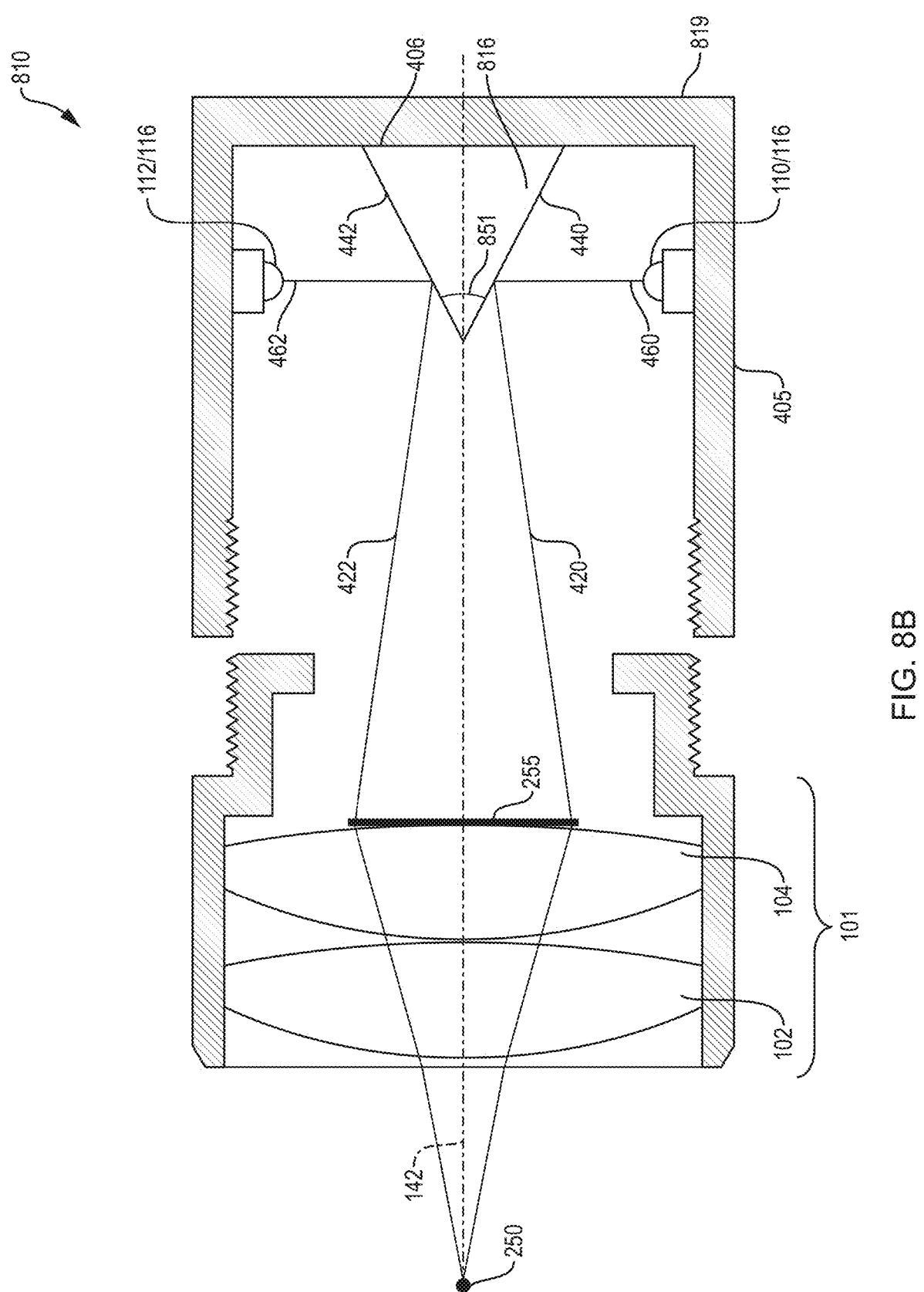

FIG. 8B illustrates a side view of a fifth aspect of the second exemplary embodiment of the lighting device shown in in FIGS. 4A-4B.

In this illustrated aspect lighting device 810 comprises lighting housing 405 comprising lens housing 101, wherein lens housing 101 includes lens 102 and 104, removably attachable to lighting housing 405, and lighting assembly 819, similar to the configuration shown in shown in FIGS. 4A, 4B, comprising lighting sources 110, 112 (or lighting modules 110/116, 112/116) positioned about an inner circumference of light assembly 819.

In accordance with the principles of operation of this illustrated embodiment, light sources 110 and 112 (or lighting modules 110/116, 112/116) are arranged along the interior surface of lighting housing 405 (or lighting assembly 818) such that light paths 460, 462 are substantially perpendicular to optical axis 142.

Further illustrated is light director 816, which is similar to light director 415, including reflective surfaces 440, 442, which reflects light projected onto reflective surfaces 440, 442, at an angle equal to the angle of the light incident to light director 816.

In this illustrated embodiment, the peak or apex angle 851 of light director 816, as shown, is an acute angle (i.e., less than 90 degrees) to enable the light emitted by lighting modules 110/116, 112/116, to be reflected toward lens assembly 101, wherein the optical characteristics of lenses 102, 104 are selected to direct the light toward point 250 (i.e., area about point 250).

Figure 9A:
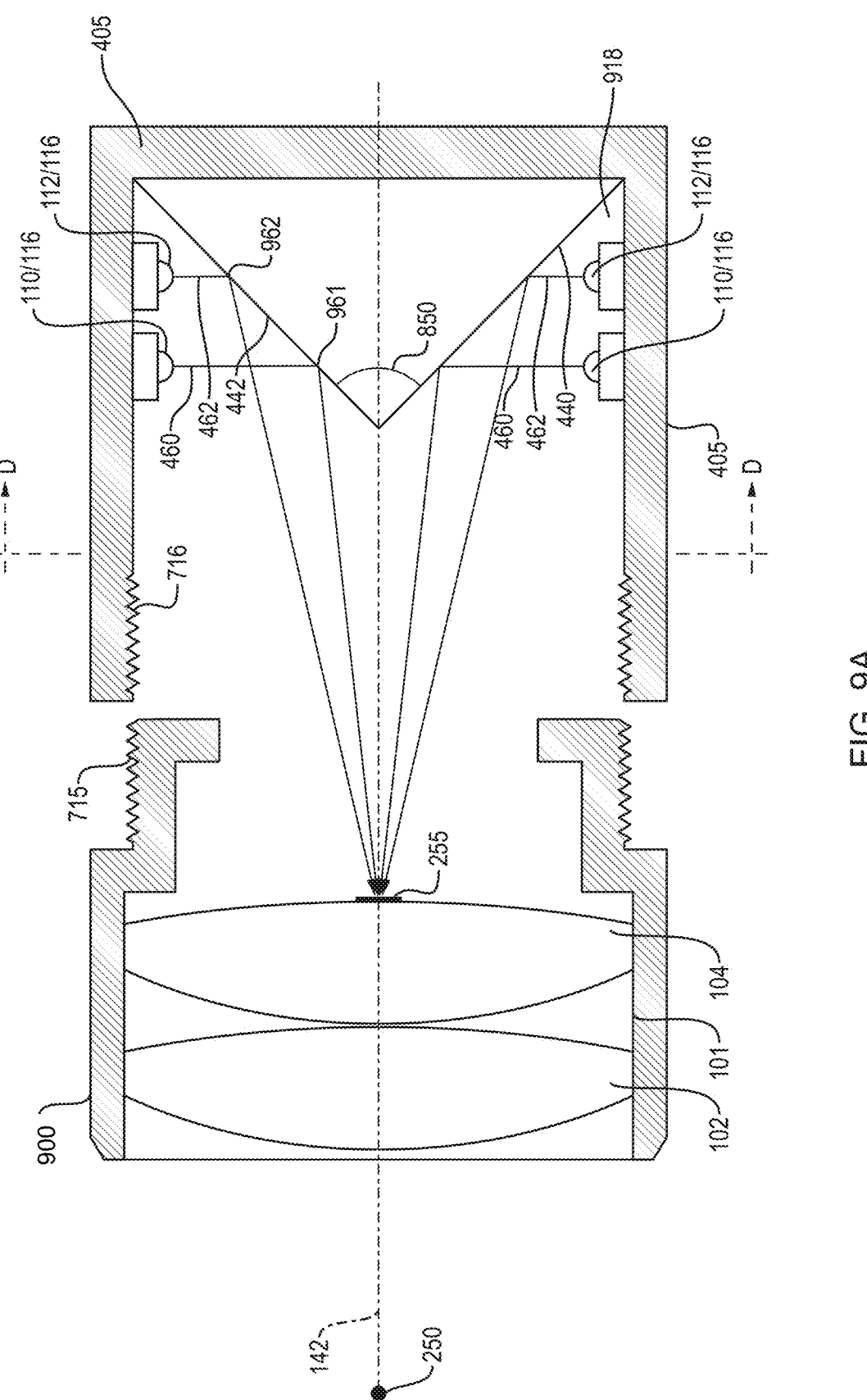
FIG. 9A illustrates a side view of a first aspect of a fifth exemplary embodiment of a lighting device in accordance with the principles of the invention.

FIG. 9A illustrates a side view of a first aspect of a fifth exemplary embodiment of a lighting device in accordance with the principles of the invention.

In this exemplary embodiment, lighting device 900, which is similar to lighting device 400, shown in FIGS. 4A, 4B, comprises a lighting housing 405 comprising lens assembly 101 comprising at least one objective lens 102, 104 and lighting assembly 918 comprising a plurality of lighting sources 110, 112 (or lighting modules 110/116,

112/116) oriented about an inner circumference of lighting housing 405 and light director 815 comprising a peak angle 850 greater than ninety (90) degrees, as discussed with regard to FIG. 8A, to redirect light contacting corresponding points on reflective surfaces 440, 442 towards region 255 on lens assembly 101. Furthermore, lens assembly 101 and lighting assembly 918 may be removably attachable to lighting housing 405, as previously discussed.

In accordance with the principles of this illustrated exemplary embodiment, lighting sources 110 and 112 (or lighting modules 110/116, 112/116) are positioned at different points along the inner circumference of lighting assembly 918, such that light emitted by lighting source 110 (or lighting module 110/116), projected along light path 460, contacts light director 815 at a first point 961 and light emitted by lighting source 112 projected along light path 462 contacts light director 815 at a second point 962.

The light emitted by lighting source 110 (module 110/116) and lighting source 112 module 112/116) is re-directed toward region 255, as previously discussed.

In one aspect of the invention a plurality of lighting sources 110 (or lighting modules 110/116) may be positioned about an inner circumference of lighting housing 405 in a first plane (in this illustrated case, the plane containing light path 460) and a plurality of second lighting sources 112 (or modules 112/116) may be positioned about an inner circumference of lighting housing 405 in a second plane (in this illustrated case, the plane containing light path 462) wherein the first point of contact 961 of light emitted by lighting source 110 on reflective surfaces 440 is within the first plane, and the second point of contact 962 of light emitted by lighting modules 112/116 on reflective surfaces 442 is within the second plane.

In one aspect of the invention, and as an example of the operation of lighting device 900, lighting sources 110 (modules 110/116) may be configured to emit a white light (i.e., violet through red wavelength ranges) while lighting sources 112 (modules 112/116) may be configured to emit light in one or more specific wavelength bands (e.g., ultra-violet, blue, green, yellow, orange, red, infra-red etc.).

In another aspect of the invention, and as a second example, lighting sources 110 (module 110/116) may comprise white light emitting elements, and selected ones of lighting sources 112 (module 112/116) may comprise lighting elements emitting light in a first wavelength range (e.g., an ultra-violet wavelength range) while selected other ones of lighting sources 112 (module 112/116) may comprise lighting elements emitting light in a different (second) wavelength range, e.g., blue wavelength range.

Figure 9B:
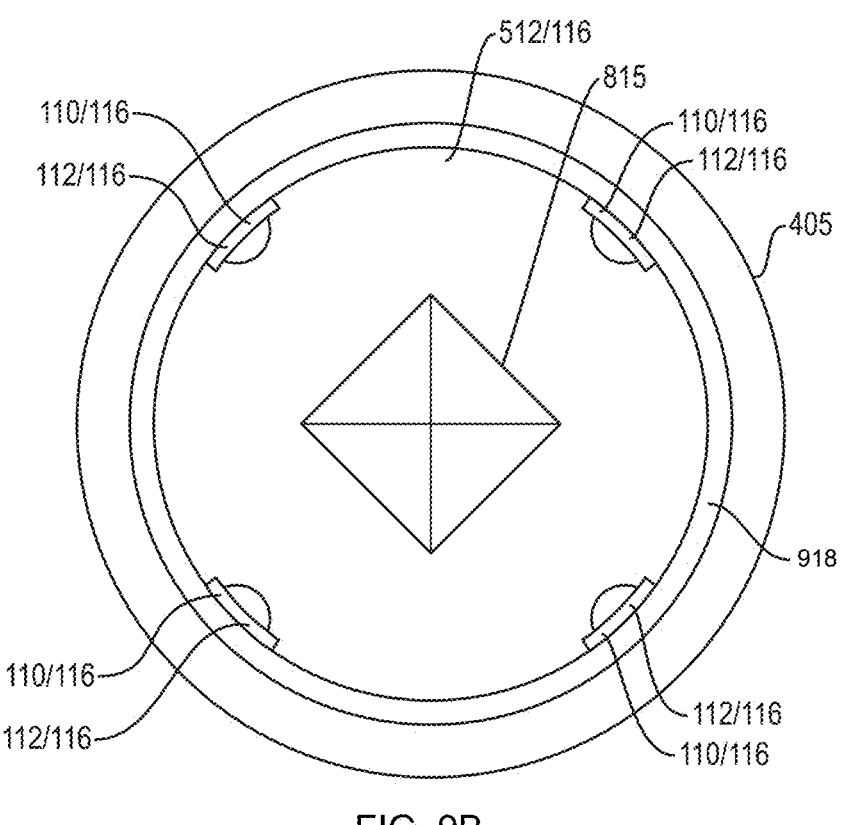
FIG. 9B illustrates a front view of the first aspect of the fifth exemplary embodiment of the lighting device shown in FIG. 9A.

FIG. 9B illustrates a front view of the first aspect of the fifth exemplary embodiment of the lighting device shown in FIG. 9A.

In this illustrated aspect, a plurality of lighting sources 110 (or lighting modules 110/116) are arranged about an inner circumference surface of lighting assembly 918 in a first plane. Similarly, a plurality of lighting sources 112 (or lighting modules 112/116) are arranged about an inner circumference of lighting assembly 918, in a second plane, as discussed with regard to FIG. 9A.

In this illustrated example, lighting modules 112/116 are not visible as these modules are positioned behind lighting modules 110/116 as the light emitted by lighting sources 110, 112 is directed toward a same surface of light director 815.

As discussed, light emitted by lighting sources 110, 112 (concurrently, individually or sequentially) is directed toward light director 815, which redirects the light toward lens assembly 101 (not shown), as previously discussed.

Although only four lighting sources 110 (or lighting module 110/116) are shown, it would be recognized that the number of lighting modules included along the inner surface of lighting assembly 418 may be increased or decreased based on the number of reflective surfaces of light director 815.

Figure 9C:
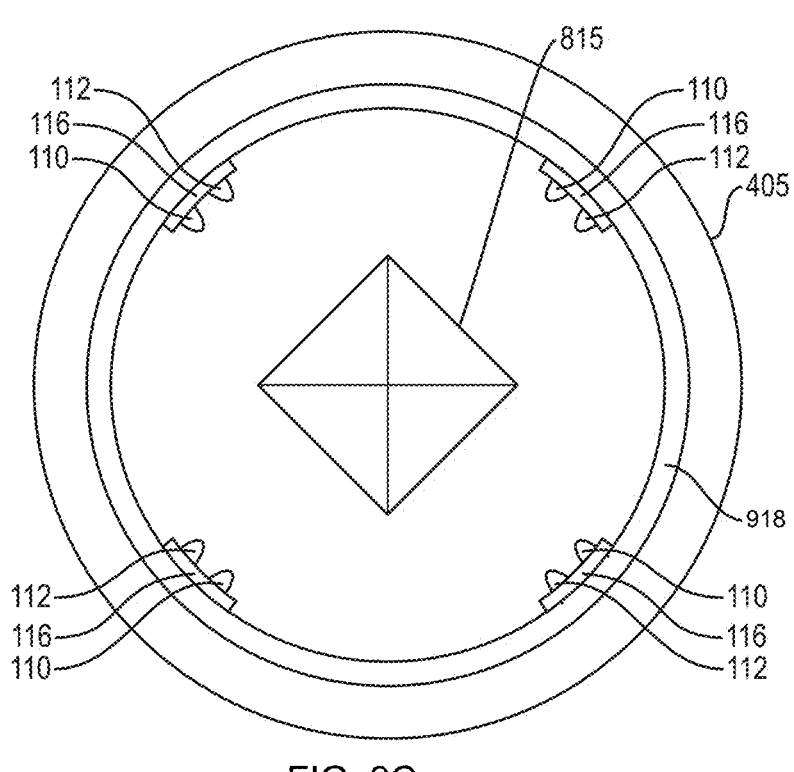
FIG. 9C illustrates a front view of a second aspect of the fifth exemplary embodiment of the lighting device shown in FIG. 9A.

FIG. 9C illustrates a front view, of a second aspect of the fifth exemplary embodiment of the lighting device shown in FIG. 9A.

In this exemplary aspect, a plurality of lighting sources 110 and 112 (or lighting modules 110/116, 112/116) are arranged as pairs about an inner circumference surface of lighting assembly 918, wherein the lighting source pair 110/112 are controlled by a same controller 116.

In this exemplary aspect, light emitted by lighting sources 110, 112 (concurrently, individually or sequentially) is directed toward light director 815, which redirects the light toward lens assembly 101 (not shown), as previously discussed.

Although only four lighting modules 110/116 are shown, it would be recognized that the number of lighting modules included along the inner surface of lighting assembly 418 may be increased or decreased based on the number of reflective surfaces of light director 815.

Although the fifth embodiment of the invention discloses is shown with regard to a prismatic structured light director 815 including an apex angle greater than ninety (90) degrees, it would be recognized that the configuration of lighting sources (or modules) shown in FIG. 9A-9C, would be applicable to the previously discussed embodiments of the invention as shown in FIGS. 4B, 7 and 8B, without altering the scope of the invention claimed.

Figure 10:
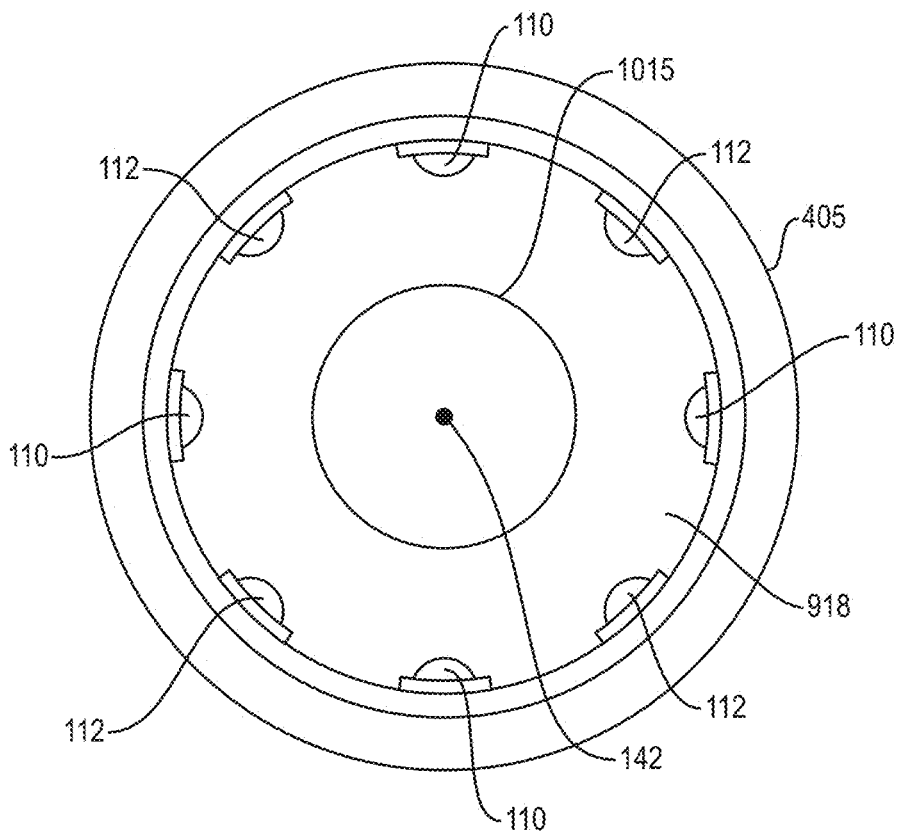
FIG. 10 illustrates a front view of a third aspect of the fifth exemplary embodiment shown in FIG. 9A.

FIG. 10 illustrates a front view of a third aspect of the fifth exemplary embodiment shown in FIG. 9A.

In this illustrated aspect of lighting device 900, lighting device 900 comprises lighting housing 405 including lens housing 101 comprising lens 102 and lighting assembly 918 comprising light director 1015, wherein light director 1015 is shown as a cone or conical element to re-direct light emitted by lighting sources 110, 112 arranged along or about an inner circumference of lighting housing 405. Conical element 1015 is advantageous as it represents a pyramid or prismatic structure of an infinite number of sides.

Lighting sources 110, shown along (or about) an inner circumference of lighting housing 405 are arranged in a first plane and lighting sources 112 shown along (or about) an inner circumference of lighting housing 405 are arranged in a second plane (similar to the configuration shown in FIG. 9B). Further illustrated are lighting source 112 offset from lighting modules 110/116.

In still a further aspect of the embodiment shown in FIG. 10, both lighting sources 110 and 112 may be arranged a same plane (i.e., the first plane and the second plane of FIG. 9B) or a single plane (FIG. 9C) wherein the plurality of lighting modules 112/116 may be offset from the lighting modules 110/116.

In accordance with this aspect of the invention, the use of conical shaped light direction 1015 allows for an increase in the number of lighting sources 110, 112 that may be utilized to project light onto focal point 250.

Although not shown, it would be recognized that prismatic structure 1015 may be constructed in a manner wherein an apex angle may be selected as one of less than ninety (90) degrees, substantially equal to ninety (90) degrees or greater than ninety (90) degrees.

Figure 11:
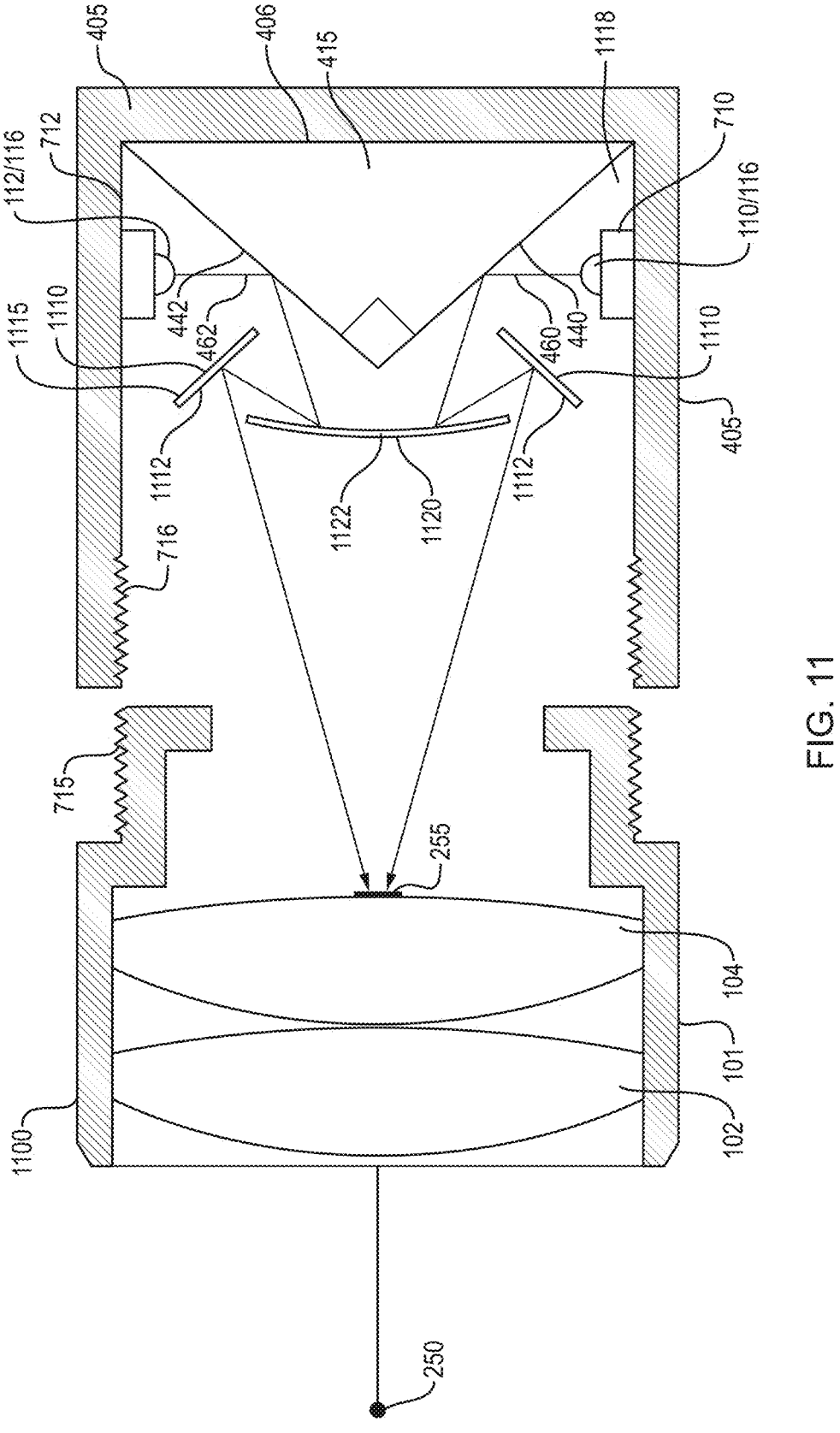
FIG. 11 illustrates a side view of a sixth exemplary embodiment of a lighting device in accordance with the principles of the invention.

FIG. 11 illustrates a side view of a sixth exemplary embodiment of a lighting device in accordance with the principles of the invention.

In this illustrated embodiment, lighting device 1110 comprises lighting housing 405, comprising lens housing 101 and a lighting assembly 1118, similar to that shown in FIGS. 4A, 4B, wherein lens housing 101 includes lens 102 and 104 and lighting housing 1118 including light director 415 and lighting sources 110 and 112. Furthermore, as discussed previously, one of lens housing 101 and lighting assembly 1118 may be removably attachable to housing 405 through one of a screw thread (715/716) a snap-fit connection, and a bayonet connection, etc.

In accordance with the principles of operation of this illustrated embodiment, lighting assembly 1118 further includes a reverse conical or parabolic element 1110 including a passthrough 1115 and conical or parabolic section 1120 positioned at or near an apex of light director 415. Reverse conical section 1110 includes reflective surface 1112 and conical section 1120 includes reflective surface 1122.

Light emitted by lighting modules 110/116, and 112/116, in this case, is re-directed toward conic section 1120, which then reflects the received light back toward reverse conical section 1110, which directs light towards lens assembly 101.

Lens assembly 101 receiving the light reflected off reflective surfaces 1112 of reverse conical section 1110 presents the re-direct light toward lenses 104, 102, which focus the light toward known point 250, as previously discussed.

Although FIG. 11 represents a configuration similar to that disclosed with regard to FIG. 4B, wherein the lighting modules 110/116, 112/116 are shown substantially perpendicular to optical axis 142 from lighting assembly 1118, it would be recognized that the principles of FIG. 11 may be applied to the configuration shown in FIGS. 7, 8A and 8B, without altering the scope of the invention claimed.

Figure 12A:
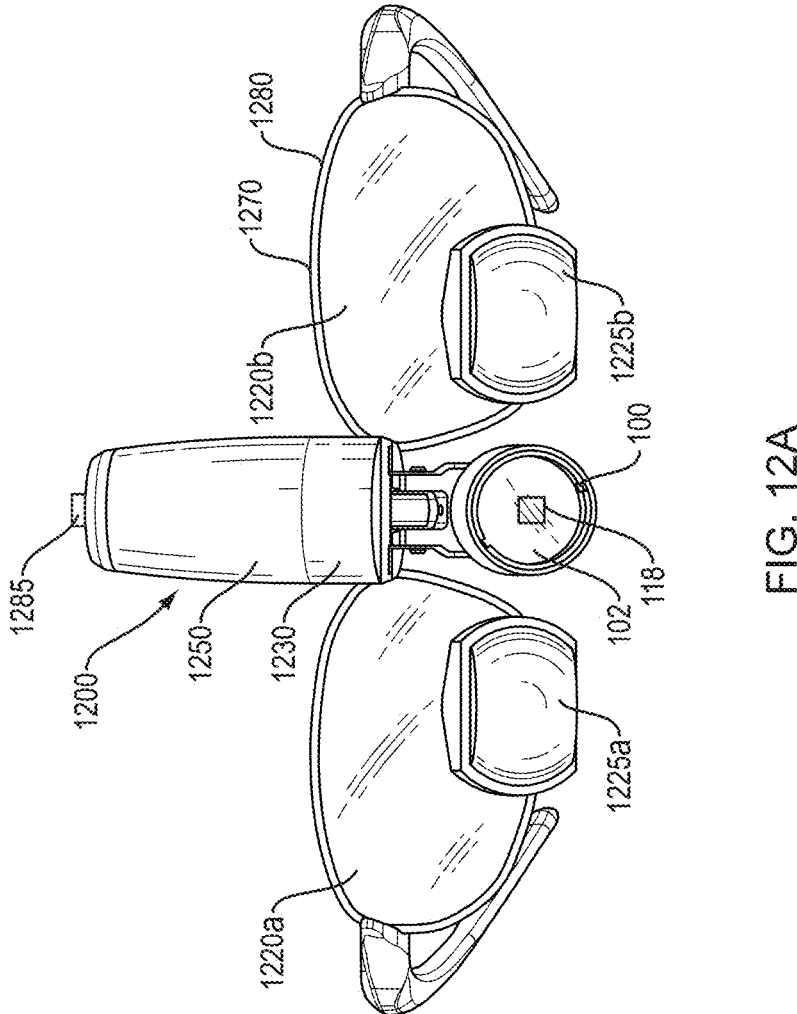
FIGS. 12A-12B illustrate a prospective view of head-mounted lighting systems utilizing a plurality of lighting devices disclosed, herein.

FIG. 12A Illustrates a front view of a head-mounted lighting configuration 1200 comprising an eyewear 1280, comprising a frame 1270 containing a left lens 1220a and a right lens 1220b into which are magnification devices 1225a, 1225b, respectively. Although the head mounted lighting device illustrated refers to an eyewear 1280, it would be understood other types of head mounted light devices are considered within the scope of the invention. For example, U.S. Pat. No. RE 46463, whose contents have been incorporated by reference, herein, illustrate head mountings, such as a head strap and headband (see FIGS. 12B, 12C), which are considered within the scope of the term "head mounted". In this illustrated example, lighting device 100 is shown suspended from eyewear 1280.

Lighting configuration 1200 further comprises a battery assembly 1250, an electronics section 1230 and a lighting device 100 as disclosed herein.

Within lighting device 100 is shown, through lens 102, lighting assembly 118 similar to that discussed with regard to FIGS. 1A and 1B.

However, it would be understood by those skilled in the art that while the lighting device 100 shown in FIG. 12A is described with regard to the embodiment of the invention shown in FIGS. 1A, 1B, it would be recognized that the other embodiments of lighting devices disclosed, herein, (e.g., 400, 500, 600, 700, 800, 900 and 1100), may be identified as lighting device 100 in relation to the configuration shown in FIG. 12A. Hence, the illustrated lighting assembly 118 may similarly be referred to as lighting assemblies 418, 518, 618, etc.

In accordance with the principles of the invention, the light output from lighting device 100 may be selected to provide one or more different light outputs based on the composition of the lighting sources incorporated into lighting modules 110/116, 112/116, etc.

Further illustrated is a sensing unit 1285 positioned along a top of battery assembly 1250. Sensing unit 1285 may be one of a contact sensor, such as a capacitive touch sensor or a contactless sensor, such as an infra-red (IR) sensor, an ultra-sonic sensor, a proximity sensor (e.g., electro-static), and other similar devices. Although not shown it would be appreciated that sensing unit 1285 may be positioned on or in electrical contact with electronics section 1230.

Battery assembly 1250 incorporates a battery, therein, (not shown) that provides power (electrical energy in the form of a voltage and/or current) to lighting device 100. Although the battery is disclosed with regard to battery assembly 1250, it would be understood that a battery or other source (e.g., AC/DC power converters) providing electrical energy to the lighting sources 110, 112 (or 512, 514), etc., for example, may be remote from the head mounted lighting device 1200. See, for example, U.S. Pat. No. RE46463, whose contents have been incorporated by reference, herein.

Electronic section 1230 includes circuitry (not shown) that controls the application of the electrical energy (i.e., voltage/current) from the battery (not shown) contained within the illustrated battery assembly 1250 to lighting assembly 118 in lighting device 100. Information from sensing unit 1285 to the circuitry within electronic section 1230 may also provide information suitable for controlling the state of the lighting modules 110/116, 112/116, etc., within lighting device 100.

In accordance with the principles of the invention, light output by one or more of the lighting modules 110/116, 112/116 (510/116, 512/116) may be controlled by operation of the sensing element 1285, for example. In one aspect of the invention, wherein each of the lighting modules 110/116, 112/116 (510, 512) generates a white light, sensing element 1285 may operate to turn ON or turn OFF the light generated by each of the modules 110/116, 112/116 (510, 512), individually, sequentially or concurrently. Similarly, in an exemplary configuration wherein first lighting module 110/116, generates light in an ultra-violet (UV) wavelength range and second lighting module 112/116 generates light in a visible (e.g., a blue, a green, a yellow, an orange, a red or a white) wavelength range, sensing element 1285 may operate to turn ON or turn OFF selected ones of the first lighting module 110/116 and second lighting module 112/116 so as to generate different light outputs.

Although a head-mounted lighting configuration 1200 illustrates an eyewear 1280 configuration incorporating magnification devices 1225a, 1225b within the lenses 1220a, 1220b, respectively, it would be recognized that the magnification devices 1125a, 1225b do not contribute to the discussion of the exemplary lighting devices disclosed, herein. And as such should be considered optional elements of lighting configuration 1200.

Figure 12B:
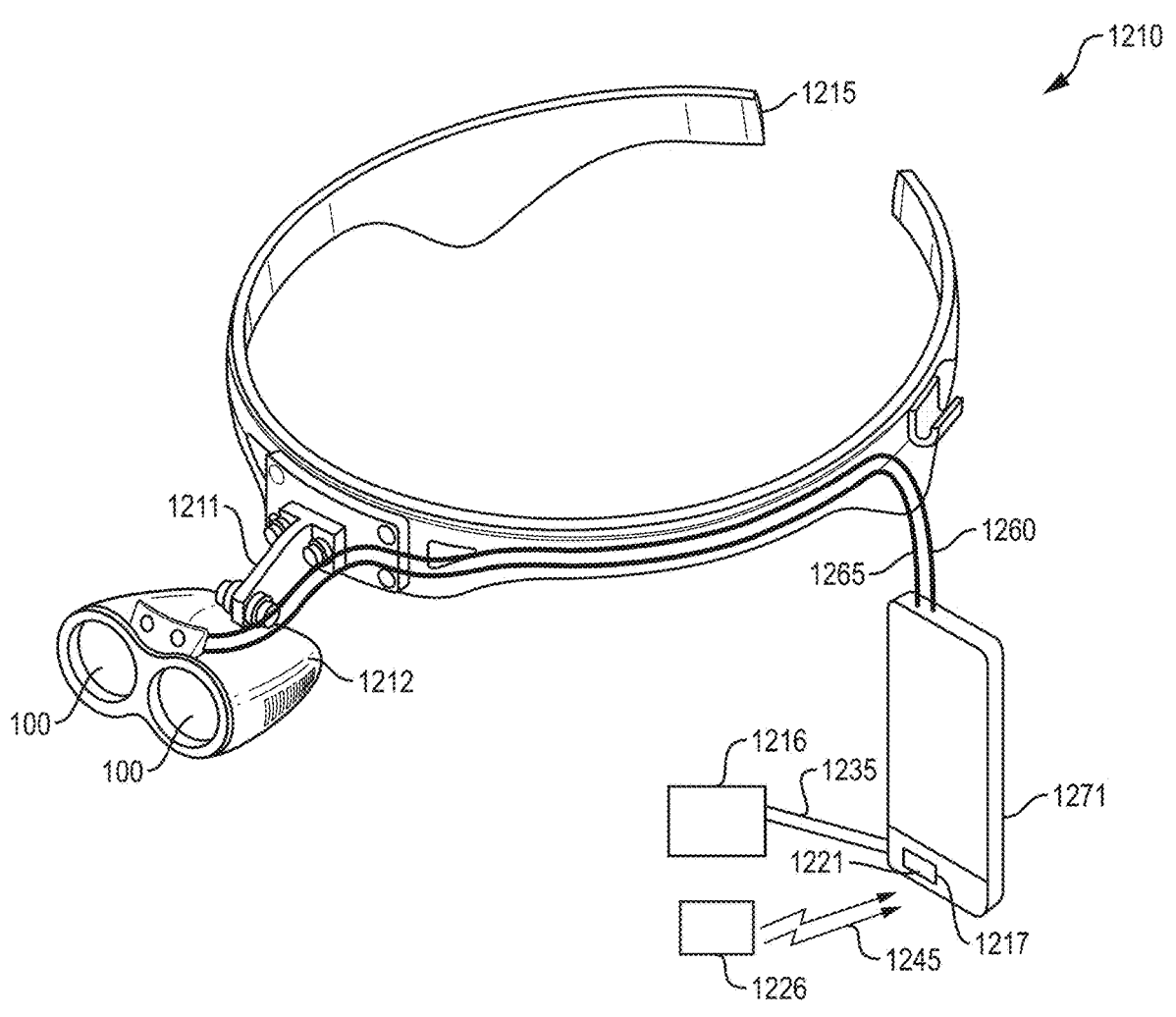

FIG. 12B illustrates a perspective view of a head-strap head-mounted lighting system 1210 including head-strap 1215 and lighting assembly 1212 suspended from head-strap by bracket 1211. Lighting assembly 1212 includes two lighting devices 100, wherein the concurrent emission of light from the two lighting devices 100 increases the amount of light that may be directed toward an area (250). In one aspect of the invention, lighting devices 100 may emit light at the same wavelength within a same wavelength band, different wavelengths within a same wavelength band or light in different wavelength bands. In still another aspect of the invention, each of lighting devices 100 may contain light sources 110, 112 (not shown) that may emit light in a same or different wavelengths bands.

Further illustrated is a power source 1271 that is electrically connected to lighting devices 100 in assembly 1212 by wired connection 1260, 1265. Distribution of electrical energy from power source 1271 may be controlled through a wired connection 1235 to switch 1215 or a wireless connection 1245 to switch 1226. Switches 1216, 1226 may comprise one of: a contact switch (toggle, electronic (e.g., capacitive touch)) or a non-contact switch (e.g., proximity switch (e.g., electrostatic, infra-red, etc.)). The wireless connection may comprise one of: a near-field communication technology or a BLUETOOTH technology. Interface 1217 on power source 1271 represents a means for electrically or electronically connecting at least one of switch 1216, 1226 to power source 1271.

Figure 12C:
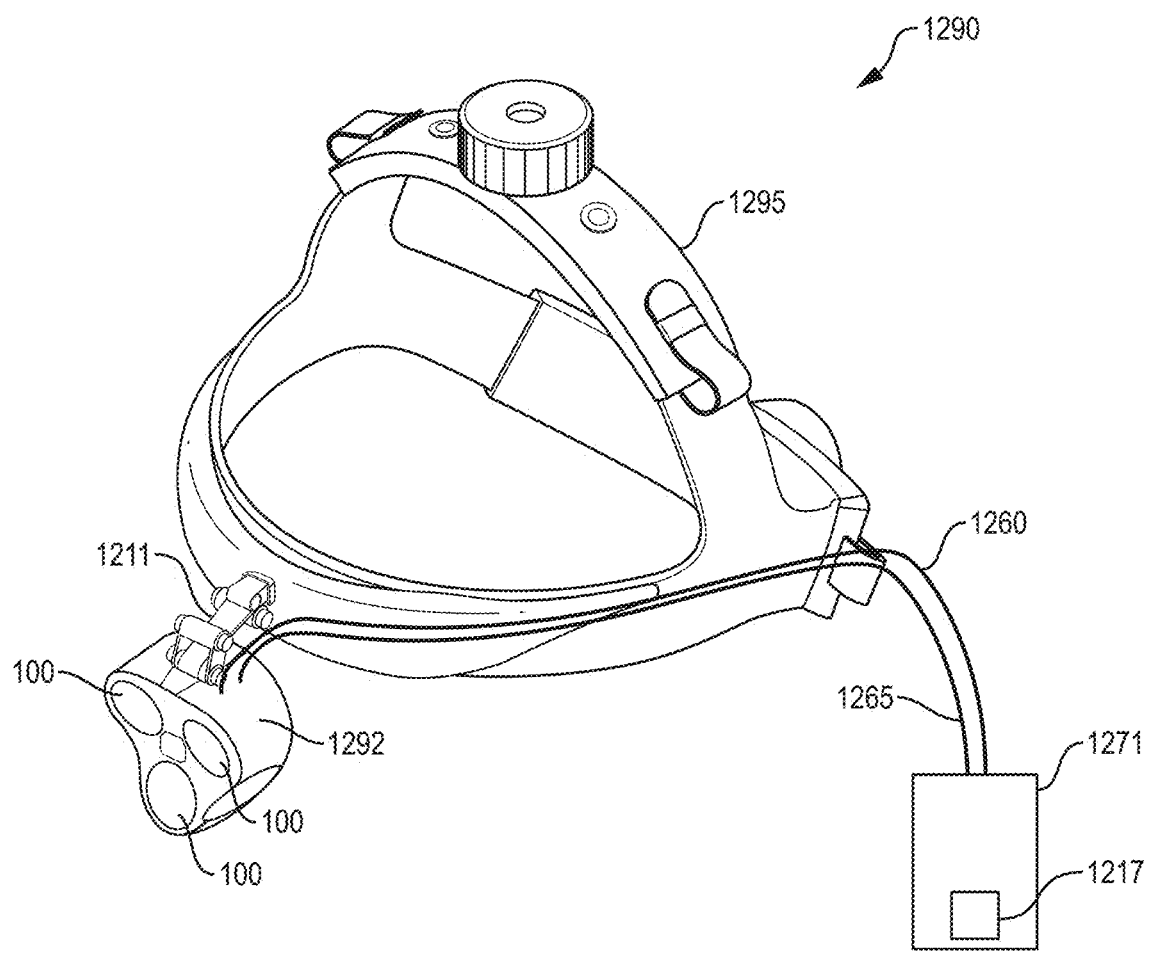
FIG. 12C Illustrates a front view of an eyewear-mounted lighting configuration incorporating a lighting device disclosed herein.

FIG. 12C illustrates a perspective view of a head-band head-mounted lighting system 1290 including head-strap 1295 and lighting assembly 1292 suspended from head-strap 1295 by bracket 1211. Lighting assembly 1292 includes three lighting devices 100, arranged about a central axis, wherein the concurrent emission of light from the three lighting devices 100 increases the amount of light that may be directed toward a common point or area (not shown). In one aspect of the invention, lighting devices 100 may emit light at the same wavelength in a same wavelength band or different wavelengths within a same wavelength band or in different wavelength bands. In still another aspect of the invention, each of lighting devices 100 may contain light sources 110, 112 (not shown) that may emit light in a same or different wavelengths bands.

Similar to FIG. 12B, power source 1271 provides electrical energy to each of the illustrated lighting devices 100 in a manner as discussed.

Figures 13A, 14:
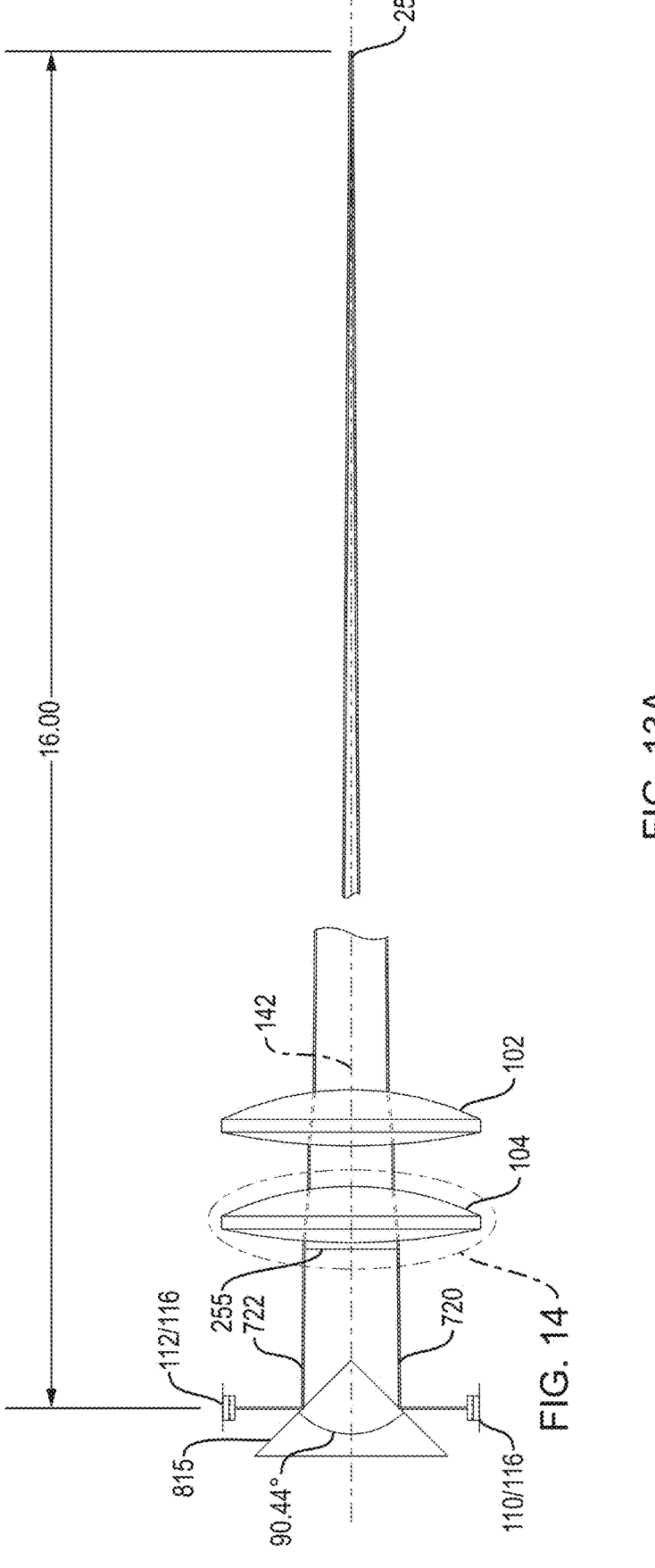
FIGS. 13A-13C illustrate cut-away side views of examples of the lighting device shown in FIG. 8A in accordance with the principles of the invention.
Figure 13B:
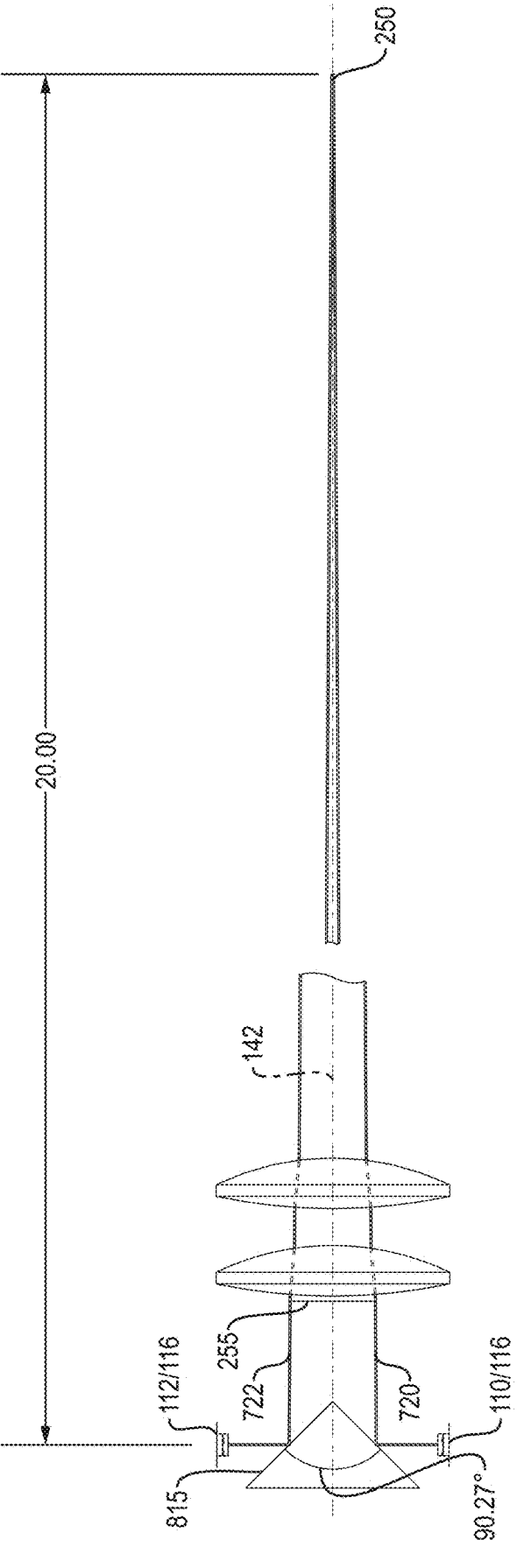
Figure 13C:
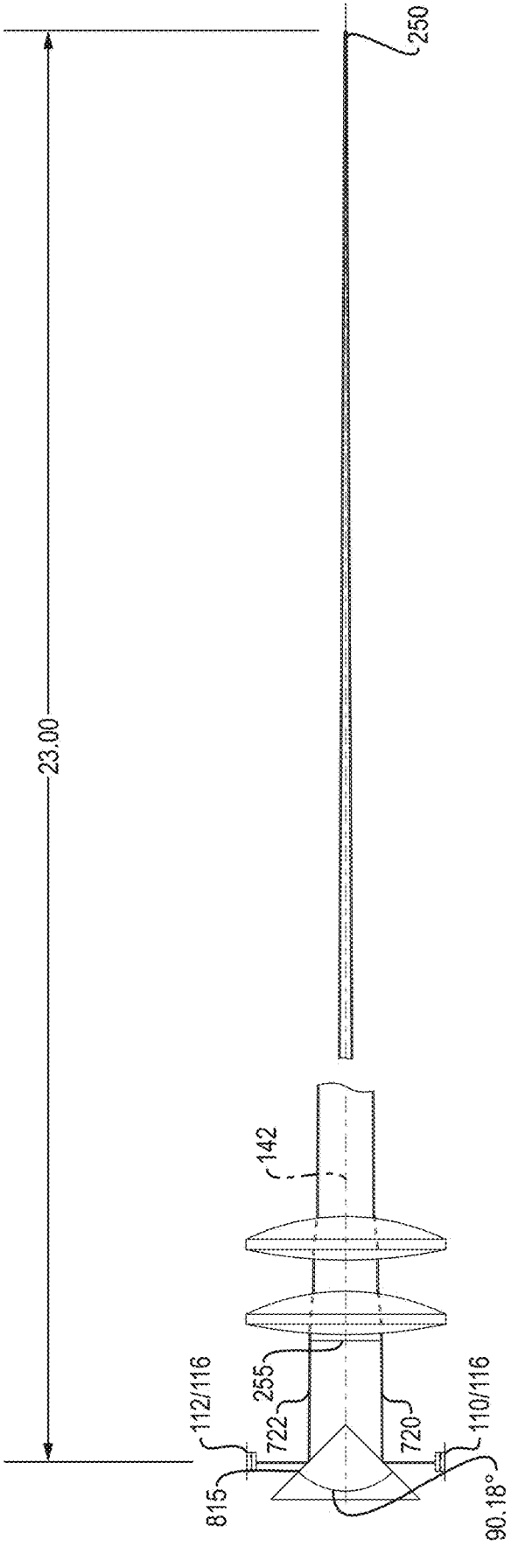

FIGS. 13A-13C illustrate cut-away side views of examples of the lighting device shown herein in accordance with the principles of the invention.

In these illustrated exemplary embodiments of lighting configurations disclosed herein, light directed toward region 255 is, after passing through lens 102, 104, is focused at a point 250 a known distance from lighting sources 110, 112; the known distance being determined in part by the illustrated apex angle associated with the illustrated light director and optical characteristics of lens 102, 104.

FIG. 13A illustrates a lighting configuration similar to that shown in FIG. 8A, wherein the apex angle of light director 815 set at 90.44 degrees (i.e., greater than 90 degrees) such that the light emitted by corresponding ones of the lighting sources 110, 112 (or lighting modules 110/116, 112/116) is re-directed toward region 255 on lens 104, 102 along optical paths 720, 722, as previously discussed.

In accordance with the principle of the invention, region 255 is selected to enable the light emitted by corresponding ones of the lighting sources 110, 112 (or lighting modules 110/116, 112/116), and re-directed by light director 815, to be focused on point 250 at a known distance from lens 102, 104 and/or lighting sources 110, 112 (or lighting modules 110/116, 112/116) after passing through lens 102, 104. In this illustrated example, light emitted by lighting sources 110, 112 (or lighting modules 110/116, 112/116) is directed along light paths 720, 722, respectively, wherein the light along light paths 720, 722 after passing though lens 102, 104 is focused onto a point 250, which is selected as 16 inches from the light sources 110, 112.

FIG. 13B illustrates a lighting configuration, similar to that shown in FIG. 8A, wherein the angle of light director

815 set at 90.27 degrees (i.e., greater than 90 degrees), such that light emitted by lighting sources 110, 112 is re-directed toward region 255 on lens 104, 102 along optical paths 720, 722, as discussed with regard to FIG. 13A.

In accordance with the principle of the invention, region 255 is selected to enable the light emitted by corresponding ones of the lighting sources 112/116, and re-directed by light director 815, to be focused on point 250 a known distance from lens 102, 104 and/or lighting sources 110, 112. In this illustrated example, light emitted by lighting sources 110, 112 (or lighting modules 110/116,112/116) is focused onto point 250, which in this illustrated example is selected as 20 inches from the light sources 110, 112.

FIG. 13C illustrate a lighting configuration, similar to that shown in FIG. 8A, wherein the angle of light director 815 set at 90.18 degrees (i.e., greater than 90 degrees), wherein the illustrated angle is set to re-director light toward region 255 on lens 104, 102 along optical paths 720, 722, as discussed with regard to FIG. 13A.

In accordance with the principle of the invention, region 255 is selected to enable the light emitted by corresponding ones of the lighting sources 110, 112 (or lighting modules 110/116, 112/116), and re-directed by light director 815, to be focused on point 250 at a known distance from lens 102, 104 or lighting sources 110, 112. In this illustrated example, light emitted by the lighting sources 110, 112 is focused onto point 250, which in this illustrated example is selected to be 23 inches from the light sources 110, 112.

Although apex angles greater than ninety (90) degrees are illustrated, it would be recognized that apex angles may be substantially equal to, or less than, ninety (90) degrees, as shown in FIGS. 4B and 8B, without altering the scope or understanding of the invention claimed.

Figure 14A:
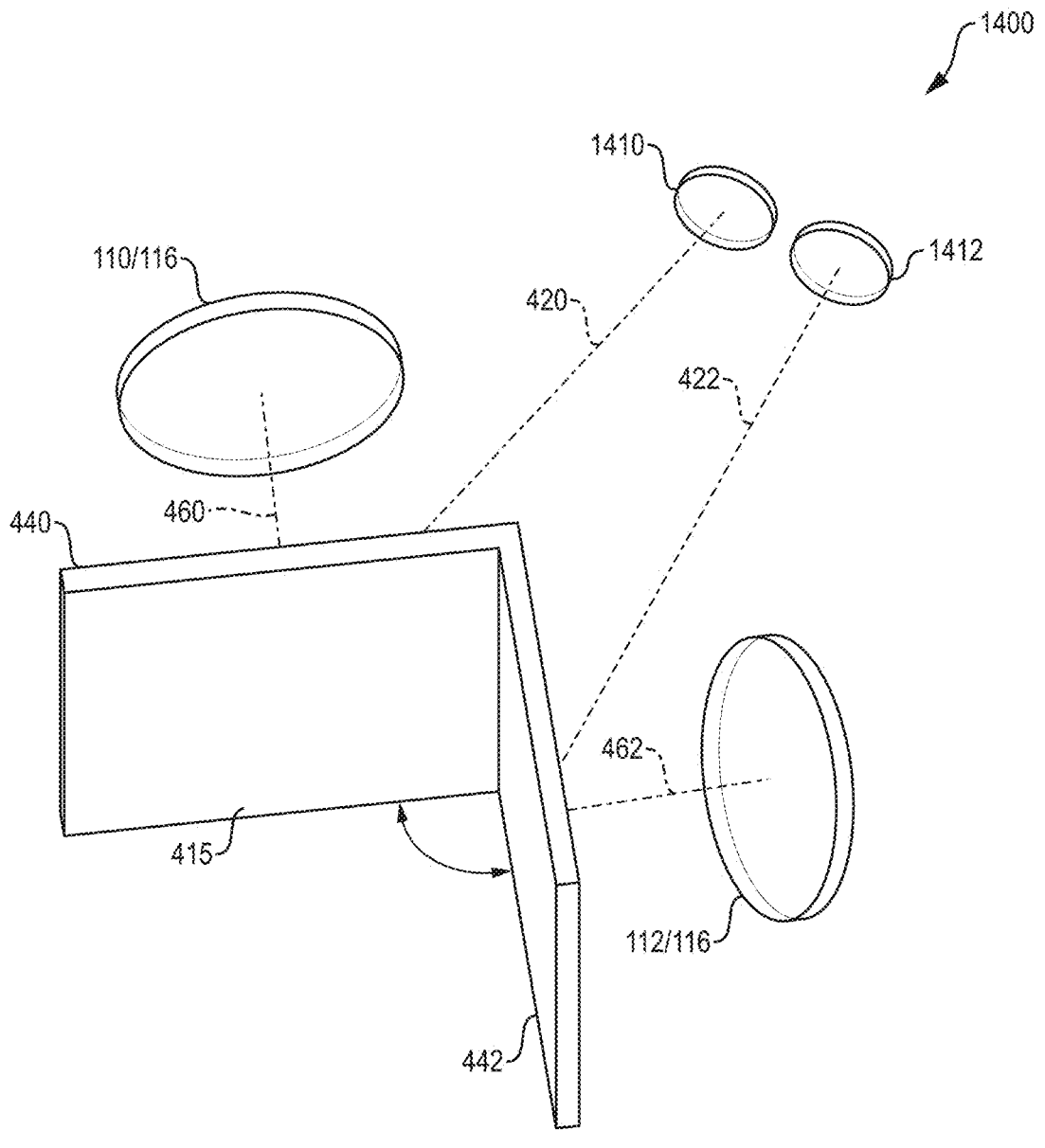
FIG. 14A illustrates a perspective view of an exemplary light distribution associated with the lighting configuration shown in FIG. 4B.

FIG. 14A illustrates a perspective view of an exemplary light distribution associated with the lighting configuration shown herein.

In this illustrated example of light distribution associated with the configuration shown in FIG. 4B, prismatic structure 415 is represented as two elements 440, 442, each containing a reflective surface, joined together at an apex angle. Apex angle is shown as being substantially equal to ninety (90) degrees. Light emitted by lighting modules 110/116, 112/116 is directed toward reflective surfaces 440, 442 and re-directed substantially parallel to optical axis (not shown), as the angle of reflection of light is reflected equal to the angle of incidence of the light. In this illustrated case, the reflected light forms two distinct light regions or spots 1410, 1412 are formed. Each of light regions 1410, 1412 possess an intensity or brightness associated with the corresponding lighting sources 110, 112.

Figure 14B:
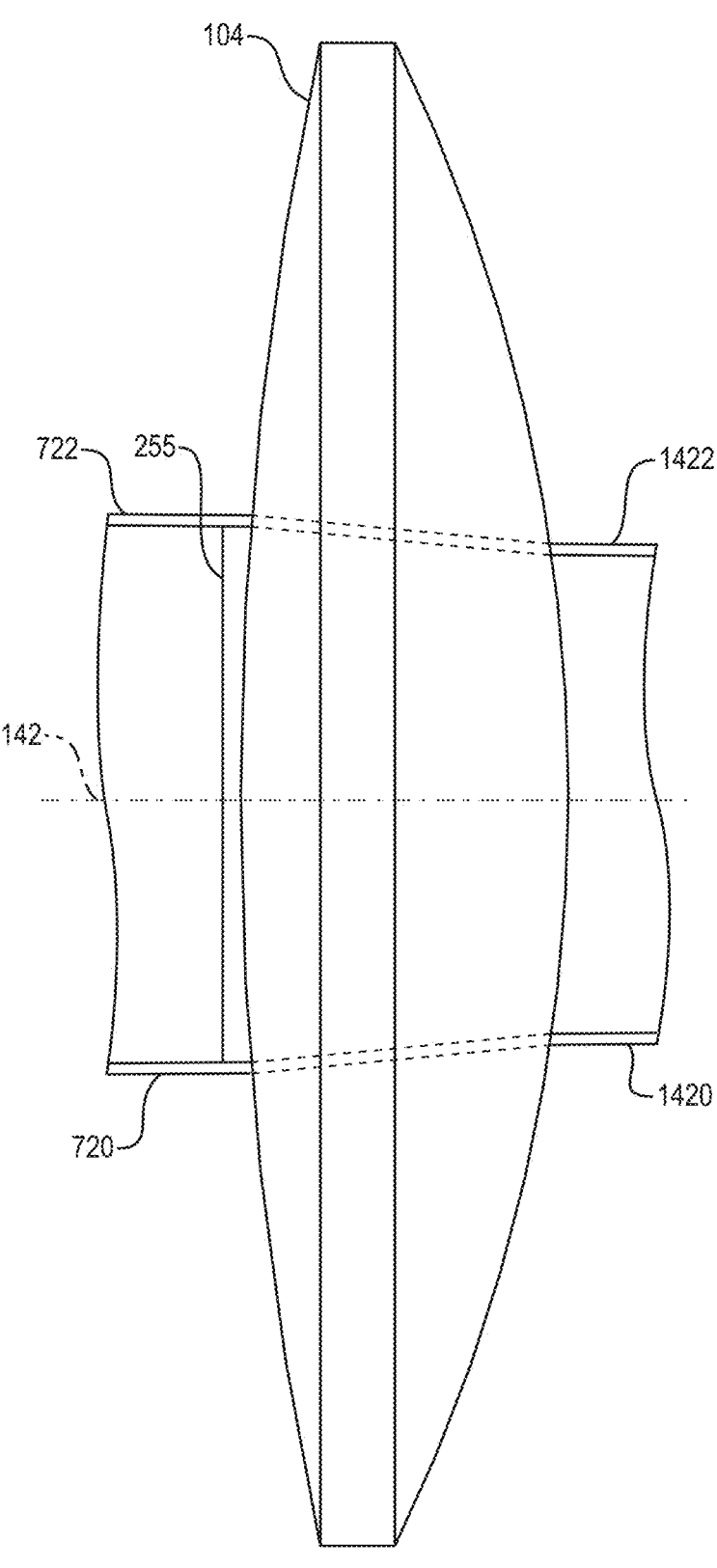
FIG. 14B illustrates an expanded view of the area identified as FIG. 14 in FIG. 13A.

FIG. 14B illustrates an expanded view of the area identified as FIG. 14 in FIG. 13A.

As would be known in the art, light, the direction of light passing through a media of different reflective indices (e.g., air-glass; glass-air) is altered with respect to an axis that is normal (i.e., perpendicular) to the lens. The degree of alteration in the direction of the path being determined by at least one optical characteristic associated with at least one objective lens. More specifically, the degree of alteration of the direction of the path of light passing through the objective lens is based on at least a ratio of the indices of reflectivity of the different media. Hence, region 255 is selected such that the direction of light travelling along optical paths 720, 722, and falling within region 255, is directed by illustrated lens 104 along light path so as to be focused onto an object or plane (not shown) at a desired distance from the lighting sources.

In this illustrated example, lens 104, for example, comprises a compound (e.g., bi-convex, aspheric, etc.) lens, wherein light passing along light paths 720, 722 is refracted, by the difference in the reflective indices of the material, to exit lens 104 along light paths 1422, 1424 that converge onto common point 250. Accordingly, light paths 1422, 1424 are shown being in a non-parallel relation with respect to optical axis 142 to allow for the convergence of light along light paths 1422, 1424 onto a point 250 (i.e., an object or plane a known distance from lens 104).

A determination of the apex angle of light directors shown herein (e.g., 815, 816) may consider at least one of:

Index of refraction of the material of the lens (i.e., optical characteristics);

a radius (power) of the lenses that the light emitted by the lights sources passes through;

a location of where the light passes through the lenses with respect to an optical axis of the lenses (i.e., optical characteristics);

an index of refraction of lenses:

a distance of the lenses with respect to the light director; and a focal lengths of the desired distance to focus the light.

Figure 14C:
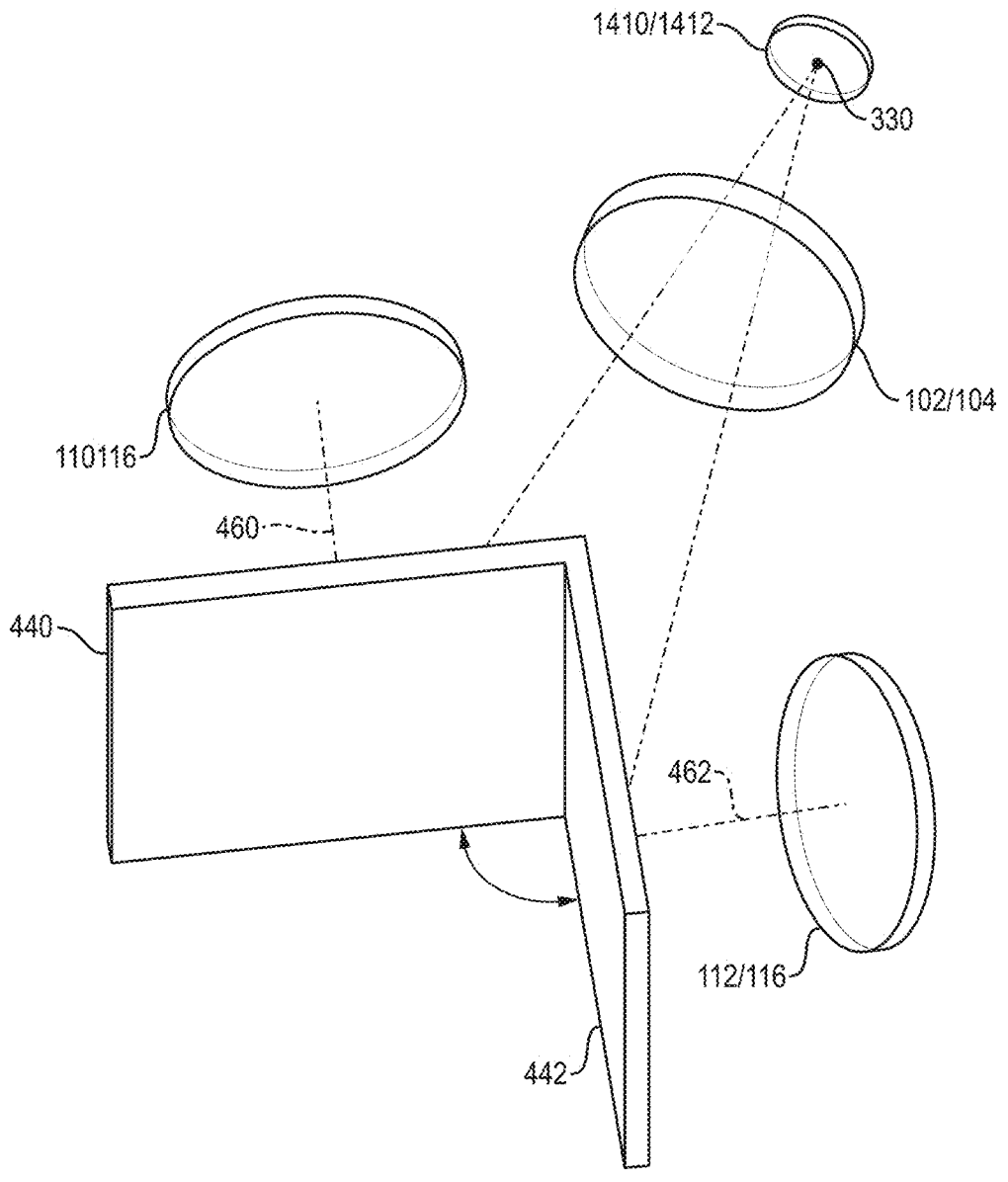
FIG. 14C illustrates a perspective view of an exemplary light distribution associated with lighting devices shown in FIG. 4B.

FIG. 14C illustrates a perspective view of an exemplary light distribution associated with the lighting configuration shown in FIG. 14A in accordance with the principles of the invention.

In this illustrated example of light distribution, the introduction of objective lens 102, 104 into the light paths associated with the light redirected from reflective surfaces 440, 442 are "bent" or redirected by the characteristics of lenses 102, 104 such that the light converges into a single light region or area substantially surrounding common point 250, a desired distance from objective lenses 102, 104.

FIG. 14D illustrates a first chart for determination of lens system power to achieve a desired level of light intensity at common point or convergence point 250.

In this illustrated chart, the exemplary embodiment of a lighting assembly similar to those shown herein, is constructed, wherein the distance to convergence point 250 is set (i.e., within measurement tolerances) to sixteen (16) inches. In this illustrated exemplary embodiment, the apex angle between reflective surfaces 440, 442 is varied as the lens power of lens assembly 101 (i.e., lenses 102, 104) is held steady. A measure of the degree of convergence of the light emitted by light sources 110, 112 at the common or convergence point 250 is obtained so as to obtain a desired (e.g., a maximum) light intensity.

As shown in FIG. 14D, with an apex angle of substantially 90 degrees (i.e., within manufacturing tolerances), convergence of the light emitted by light sources 110, 112 is not achievable with lenses 102, 104 having a combined power of less than 24.0 diopters.

However, with an angle less than 90 degrees convergence of the light emitted by light sources 110, 112 may be achieved. For example, at seventy-seven (77) degrees with lenses 102, 104 having a combined power of +8.00 diopters (i.e., 2× power), convergence of light is approximately 100 percent, and at 75 degrees with lens power of +16.00 diopters (i.e., 4× power) convergence is approximately 90 percent. Accordingly, the light beams associated with the light emitted by lighting sources 110, 112 nearly completely overlap or are focused onto an area at the desired distance of 16 inches with the appropriate selection of lens power and apex angle.

Accordingly, the light beams associated with the light emitted by lighting sources 110, 112 nearly completely overlap or are focused onto an area at the desired distance of 16 inches with the appropriate selection of lens power and apex angle.

FIG. 14E illustrates a second chart for determination of lens system power to achieve a desired level of light intensity at common point or convergence point.

In this illustrated chart, the exemplary embodiment of a lighting assembly as shown herein is constructed and common point 250 is measured at approximately twenty (20) inches from lens assembly 101. In this illustrated example, convergence of light emitted by lighting sources 110, 112 is achieved with an apex angle of 75 degrees with +16.00 diopter lens assembly power.

Accordingly, the light beams associated with the light emitted by lighting sources 110, 112 nearly completely overlap or are focused onto an area at the desired distance of 20 inches with the appropriate selection of lens power and apex angle.

Although measurements have been taken utilizing only a single lighting configuration (See FIG. 15, with lighting sources 110, 112 emitting light at the same wavelength) and at two (2) distances (16 and 20 inches) with three (3) objective lens powers, it would be recognized that the method disclosed, herein, for determining an apex angle/lens power combination that achieves substantially 100 percent convergence (i.e., nearly completely overlap) of the beams of light emitted by separate lighting sources 110, 112 would be applicable to different combinations of lighting configurations, without altering the scope of the invention.

In addition, the illustrated examples of lens power/peak angle configuration are based on a single, desired, distance (D) between the peak angle of the light director and the lens assembly 101. One skilled in the art would recognize that other distances (D) between the peak angle and the lens assembly 101 may be utilized without altering the scope of the invention claimed. In the illustrated case shown in FIGS. 14D and 14E, the distance D is selected to limit an overall length of a lighting device, wherein the lens power is increased. However, as the distance D increases, it would recognized that the necessary lens power may be altered for different peak angle configurations.

Hence, those skilled in the art would recognize and understand that a further tradeoff study may be undertaken to determine a distance (D), peak angle and lenses power combination that achieves an optimal or desired configuration for an overall length of a lighting device. Such tradeoff study is considered to be within the scope of the invention claimed.

Although light convergence is discussed in the context of determining a desired configuration, it would be recognized the size of the area of convergence of the emitted light may also be considered. In this case, the beamwidth of the lighting sources 110, 112 may further be a variable to be taken into consideration.

In addition, the optical power of the lenses within the lens assembly may be selected based on the achieving a desired intensity with a known area (e.g., 100% convergence) or achieving a desired illuminated size of the known area (e.g., less than 100% convergence). That is, a greater spot size may be achieved, wherein intensity in the middle of the area is greatest (e.g., two beams of light converging) while intensity falls off toward the edges of the area (e.g., single beam of light).

Figure 15:
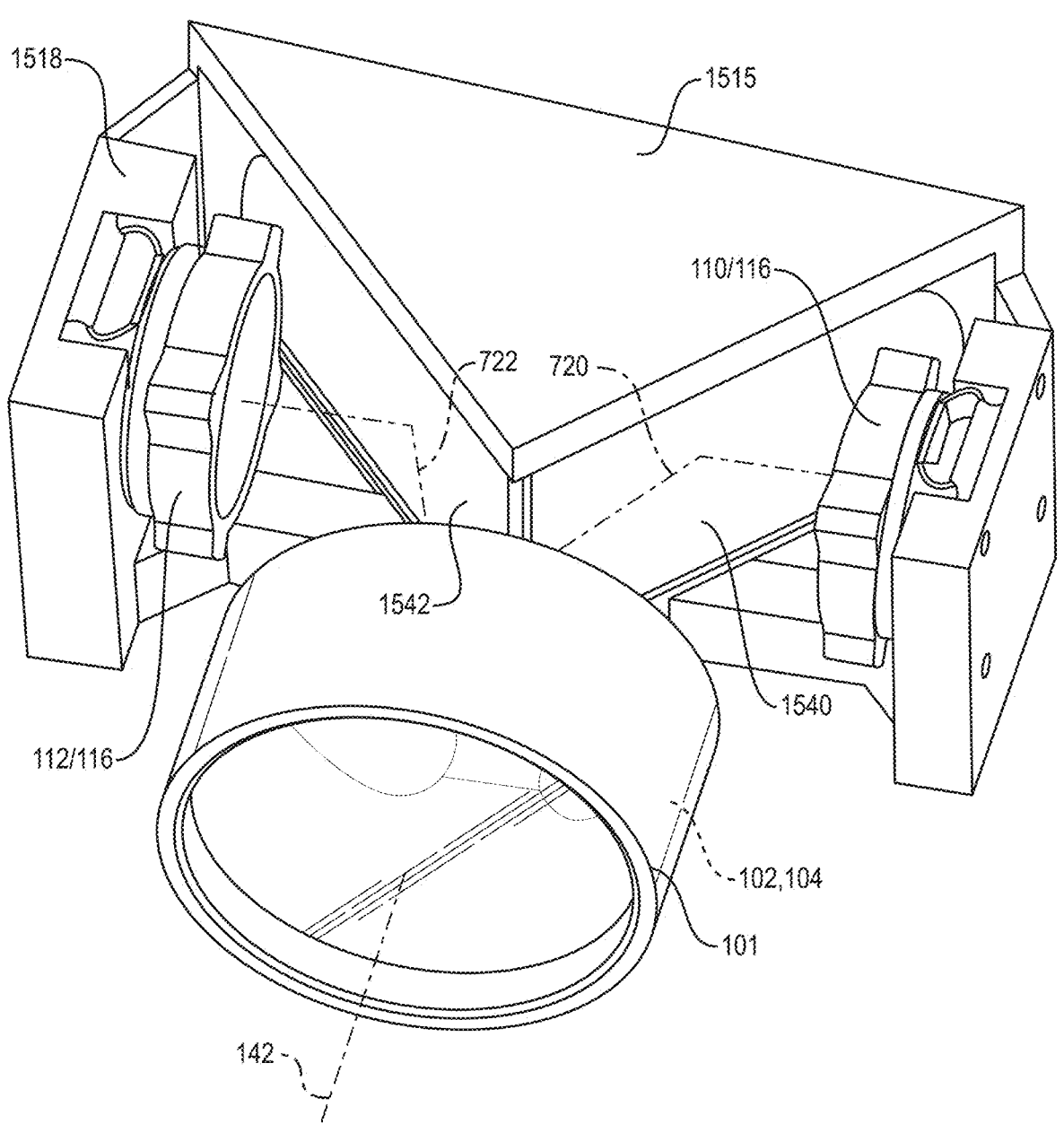
FIG. 15 illustrates a perspective view of a second aspect of a light director as shown in FIG. 8B.

FIG. 15 illustrates a perspective view of a test rig for determining a lighting configuration in accordance with the principles of the invention In this illustrated aspect, light director 1515 comprises lighting assembly 1518 comprises a plurality of reflective surfaces 1540, 1542, which include at least one of a mirror surface and a highly polished metal surface (e.g., aluminum), etc.) arranged in an angular relationship extending from base of lighting assembly 1518 at an angle. In one aspect of the invention, the plurality of reflective surfaces 1540, 1542 may extend from the base at an angle such that an obtuse (greater than 90 degrees), an acute (less than 90 degrees), or right (90 degrees) apex angle may be formed. Further illustrated are a plurality of lighting sources 110, 112 (or lighting modules 110/116, 112/116) arranged on an inner circumference of assembly 1518 (not shown), such that light projected by lighting sources 110, 112, is substantially perpendicular to optical axis 142, similar to the configuration shown in FIG. 8A.

In accordance with this aspect of the invention, light director 1515 comprises surfaces 1540, 1542 (which are similar to reflective surfaces 440, 442) arranged such that angle (i.e., an apex angle) between surfaces 1540, 1542 is ninety (90) degrees.

In this aspect of the invention, light emitted by lighting modules 110/116, 112/116 (is re-directed by surfaces 1540, 1542 toward lens assembly 101 (i.e., lenses 102, 104) and converged onto point 250, a known distance from lens assembly 101 as discussed herein. The selected angle of the highly reflective surfaces 1540, 1542 may be fixed in place by an adhesive (e.g., epoxy) to retain reflective surfaces 1540, 1542 in place.

Although the light director 1515 is discussed as being comparable to the light director 815 and the lighting sources 110, 112 configurated shown in FIG. 8A, it would be recognized that configuration of light director 1515 (i.e., a plurality of highly reflective surfaces) would be applicable to the configuration shown in FIGS. 8A and 8B, wherein the apex angle between surfaces 1540, 1542 is a perpendicular angle and the lighting sources 110, 112 are arranged at an angle with respect to the optical axis 142 (not shown). Similarly, the illustrated configuration shown in FIG. 15 would be application to the configuration shown in FIG. 8B.

Furthermore, although surfaces 1540, 1542 are illustrated as being planar, it would be within the knowledge of those skilled in the art to incorporate surfaces that are spherical or parabolic to direct light as discussed herein.

Although the configuration shown in FIG. 15 is discussed with reference to FIG. 8A, it would be understood by those skilled in the art that the principles discussed with regard to FIGS. 7 and 8B would be applicable to a configuration of a light director as discussed with regard to FIG. 15.

Figure 16:
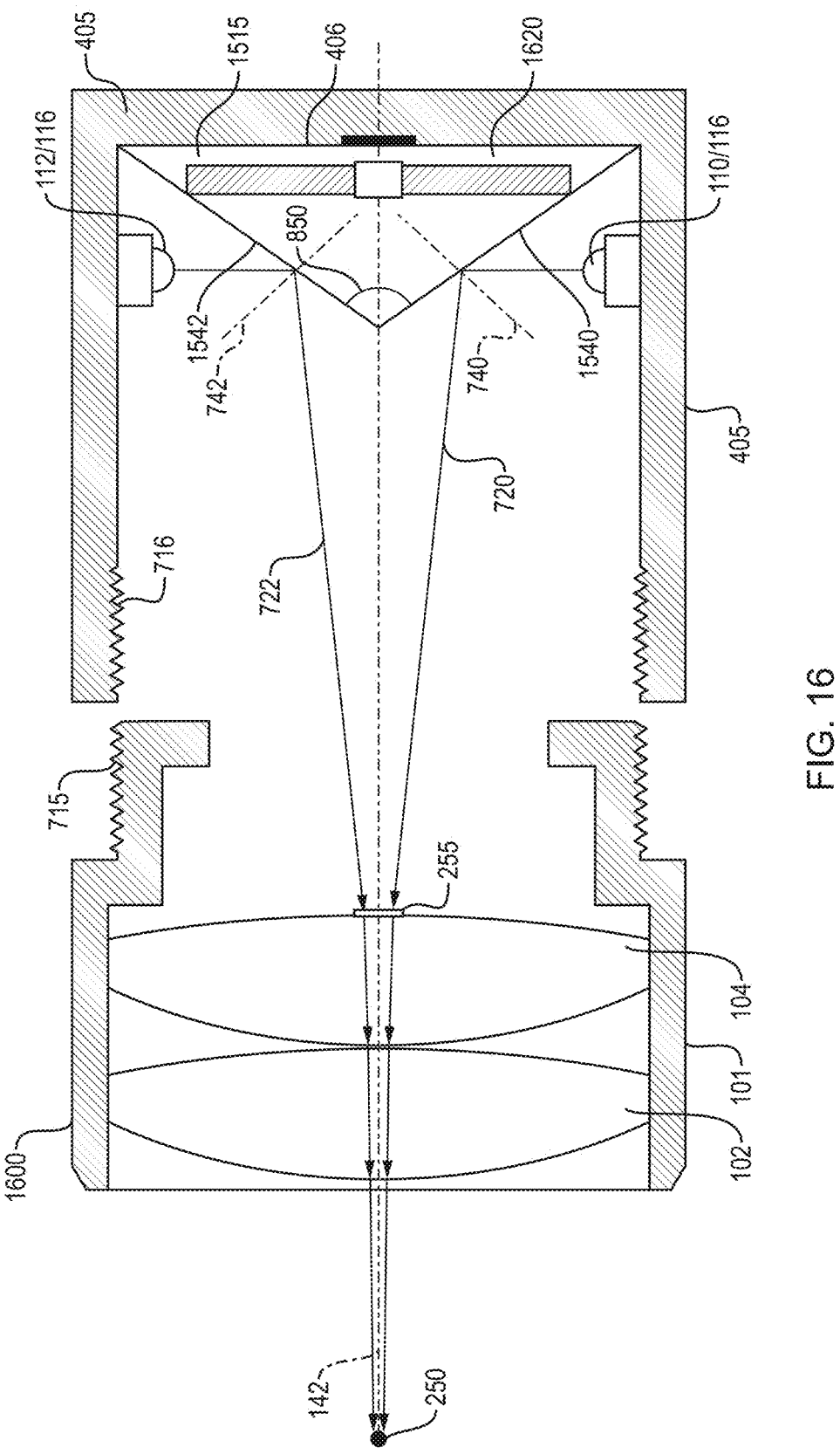
FIG. 16 illustrates a top view of the exemplary embodiment of the lighting device shown in FIG. 15.

FIG. 16 illustrates a top view of the exemplary embodiment of the lighting assembly 1518 shown in FIG. 15.

In this illustrated view, reflective surfaces 1540, 1542, extending from a base of assembly 1518 are joined together to form an apex angle 850.

Further illustrated is an adjustment mechanism 1620 positioned between the reflective surfaces 1540, 1542. Adjustment mechanism 1620 may be configured to alter the orientation of reflective surfaces 1540, 1542 with respect to each other, such that apex angle 850 between the reflective surfaces 1540, 1542 may be altered.

In one aspect of the invention, adjustment mechanism 1620 may comprise a screw thread that allows for the expansion or contraction of apex angle 850 formed by surfaces 1540, 1542. After a desired apex angle is achieved, reflective surfaces 440, 442 may be retained in place by an epoxy.

Accordingly, one skilled in the art would, with the adjustment device shown in FIG. 16, may determine apex angle 850 with respect to focusing light onto point 250, when one or more of the distance to point 250 is changed or when one or more of the characteristics of the lens 102, 104 in lens assembly 101 is changed.

Although, the adjustment device shown in FIG. 16 is presented as a screw thread device, it would also be known in the art that the housing containing the plurality of reflective elements may be prefabricated to position the reflective elements at a known angle when the optical characteristics of the at least one lens is known and fixed.

Figure 17:
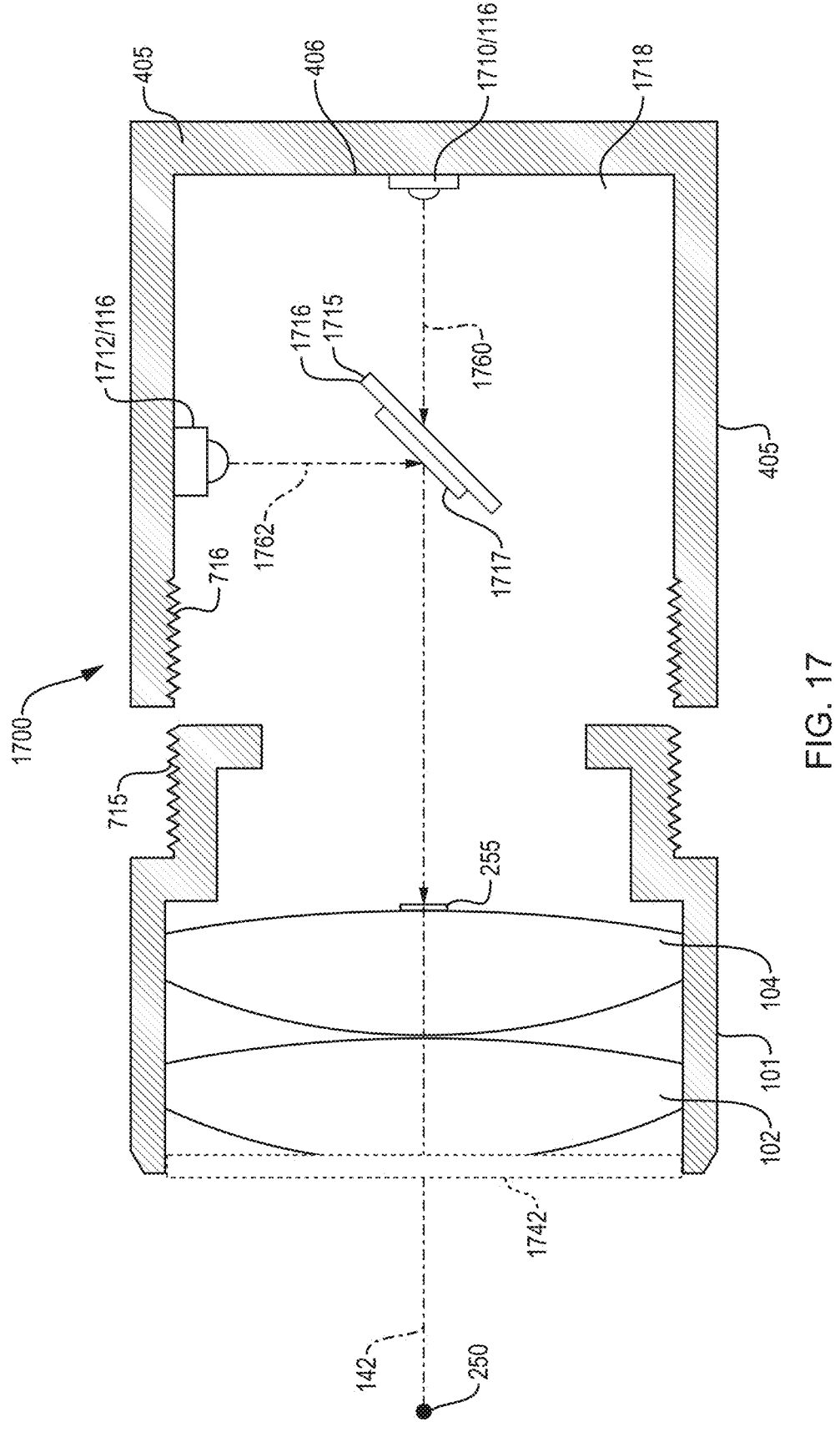
FIG. 17 illustrates a cut-away side view of a seventh exemplary embodiment of a lighting device comprising multiple lights sources in accordance with the principles of the invention.

FIG. 17 illustrates a cut-away side view of a seventh exemplary embodiment of a lighting device comprising multiple lights sources in accordance with the principles of the invention.

In this illustrated embodiment of light device 1700, which is similar to that discussed with regard to FIGS. 7, 8A and 8B, comprises lens housing 101 including lens 102, 104 and lighting housing 405, which comprises lighting assembly 1718. Lighting assembly 718 comprises a plurality of lighting sources 1710, 1712 (or lighting modules 1710/116, 1720/116, which are comparable to lighting sources 110, 112, previously discussed. Further illustrated is light director 1715, which is orientated at a 45 degree angle with respect of base 405.

In accordance with the principles of this exemplary embodiment of the invention, lighting sources 1712 (or lighting module 1712/116) is positioned along an inner circumference of assembly 1718 and lighting source 1710 (or lighting module 1710/116) is positioned on base element 405 of light assembly 1718, substantially along optical axis 142. Accordingly, light emitted by lighting source 1710 is projected along optical axis 142 toward point 250. In one aspect of the invention, lighting source 1710, similar to lighting source 110, may emit a white light, which lighting source 1712, similar to lighting source 112, may emit a non-white light (e.g., Ultra-violet, blue, red, infra-red, etc.)

Light director 1715 comprises reflective surface 1716 configured to receive light 1762 emitted by lighting source 1712, and re-direct the emitted light along optical axis 142, wherein light emitted by lighting sources 1710 and 1712 are combined into a single light projected along optical axis 142.

In addition, reflective surface 1716 may include an optical coating 1717, which allows for the transmission of light 1760 emitted by lighting source 1710 (or lighting module 1710/116), such that light from lighting sources 1710, while reflecting light emitted by lighting source 1712. In this manner light emitted by lighting sources 1710 and 1712 are projected onto common point 250 positioned along the optical axis 142.

Accordingly, light director 1715 operates as a beam combiner to allow the transmission of 100 percent of the light emitted by lighting source 1710 and 100 percent of the light emitted by lighting source 1712 to be directed along optical axis 142.

In one aspect of the invention, optical coating 1717 may further include a filter characteristic that may be utilized to structure or limit a wavelength range of the light emitted by lighting device 1700. In an alternative configuration, lighting device 1700 may include filter 1742 positioned on a distal end of lighting device 1700. Filter 1742, similar to the filter characteristics of optical coating 1717 may be utilized to structure or limit a wavelength range of the light emitted by lighting device 1700.

Although FIG. 17 is discussed with regard to a configuration wherein a white light source is positioned on base 406 and a non-white source is positioned on an inner circumference of housing 405, it would be within the knowledge of those skilled in the art to alter the positioning of the lighting sources to achieve a combined light output based on the teachings of the invention presented herein.

Figure 18:
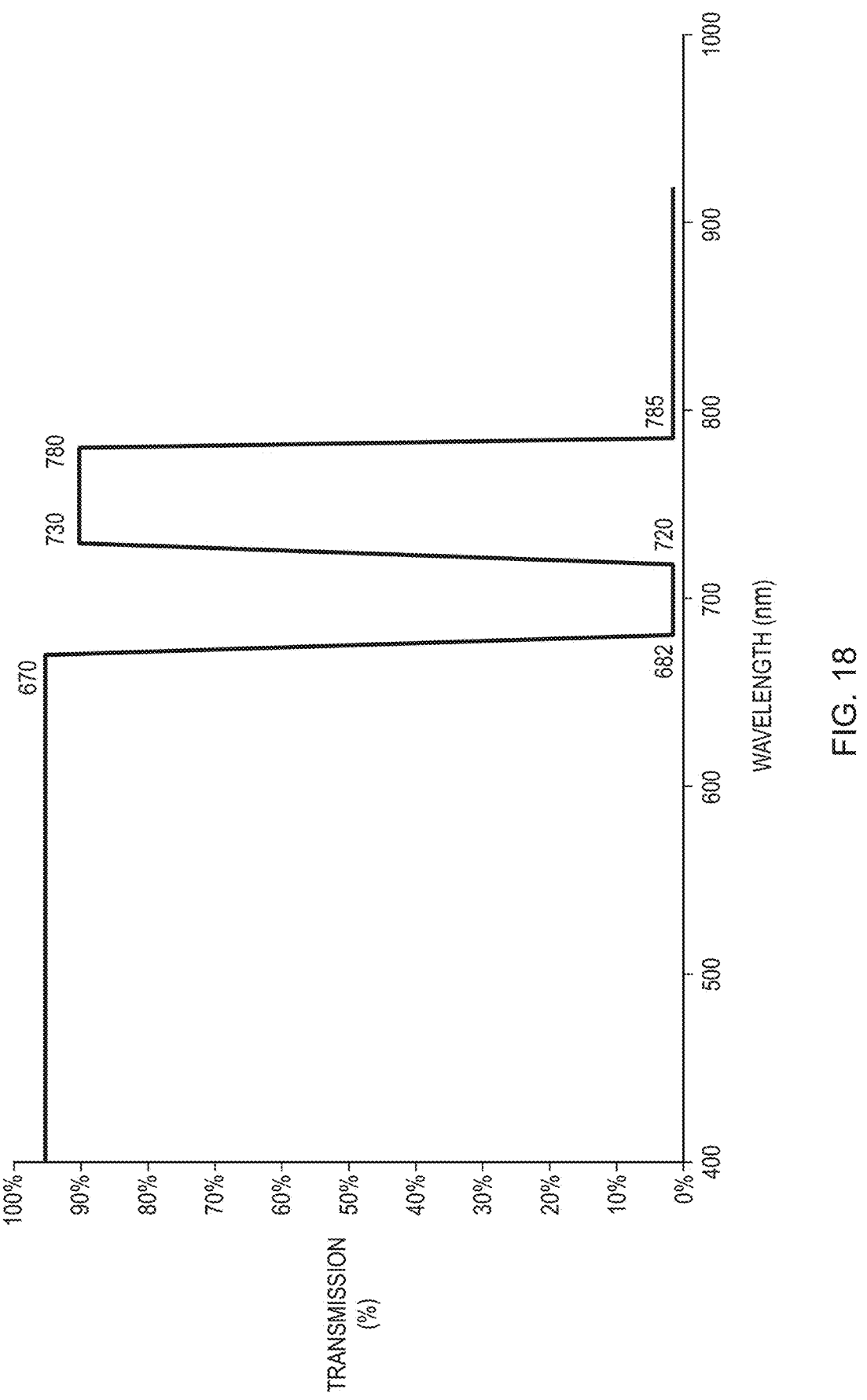
FIG. 18 illustrates a graph of an exemplary filtering of light emitted from lighting device 1700.

FIG. 18 illustrates a graph of an exemplary filtering of light emitted from lighting device 1700.

In this illustrated example, optical coating 1717 (or filter 1742) shown in FIG. 17, is configured to allow the passage of light emitted by device 1700 to a first wavelength range, wherein the first wavelength is in range of 400 and 670 nm. Hence, while lighting source 1710 may emit a white light (i.e., 400-700 nm), the light emitted by lighting device 1700 is limited to a range of 400-670 nm. In addition, optical coating 1717 (or filter 1742) may be further configured to allow passage of light within a range of 730-780 nm. Hence, while lighting source 1712 may emit an infra-red light (wavelengths greater than 700 nm), filter 1742 may limit the light emitted by lighting device 1700 to be within a range of 730-780 nm.

Thus, the light projected onto point 250 is limited to wavelength ranges that are allowed to pass through coating 1717 and/or filter 1742.

In one aspect of the invention, a combination of coating 1717 and filter 1742 may be utilized to allow passage or emission of a light having desired wavelength ranges for the combination of light.

In this illustrated example, the wavelength ranges associated with coating 1717 (or filter 1742) are chosen to describe the optical characteristics of the coating or filtering. It would be within the knowledge of those skilled in the art to select other band-pass wavelength configurations without undue experimentation to achieve a light emitted by the devices discussed, herein, to have other desired wavelength characteristics.

Although the use of optical coating and filters is disclosed with regard to lighting device 1700, it would be recognized that the principles of the illustrated optical coating and/or filtering may be applied to each of the lighting devices disclosed herein.

Figure 19:
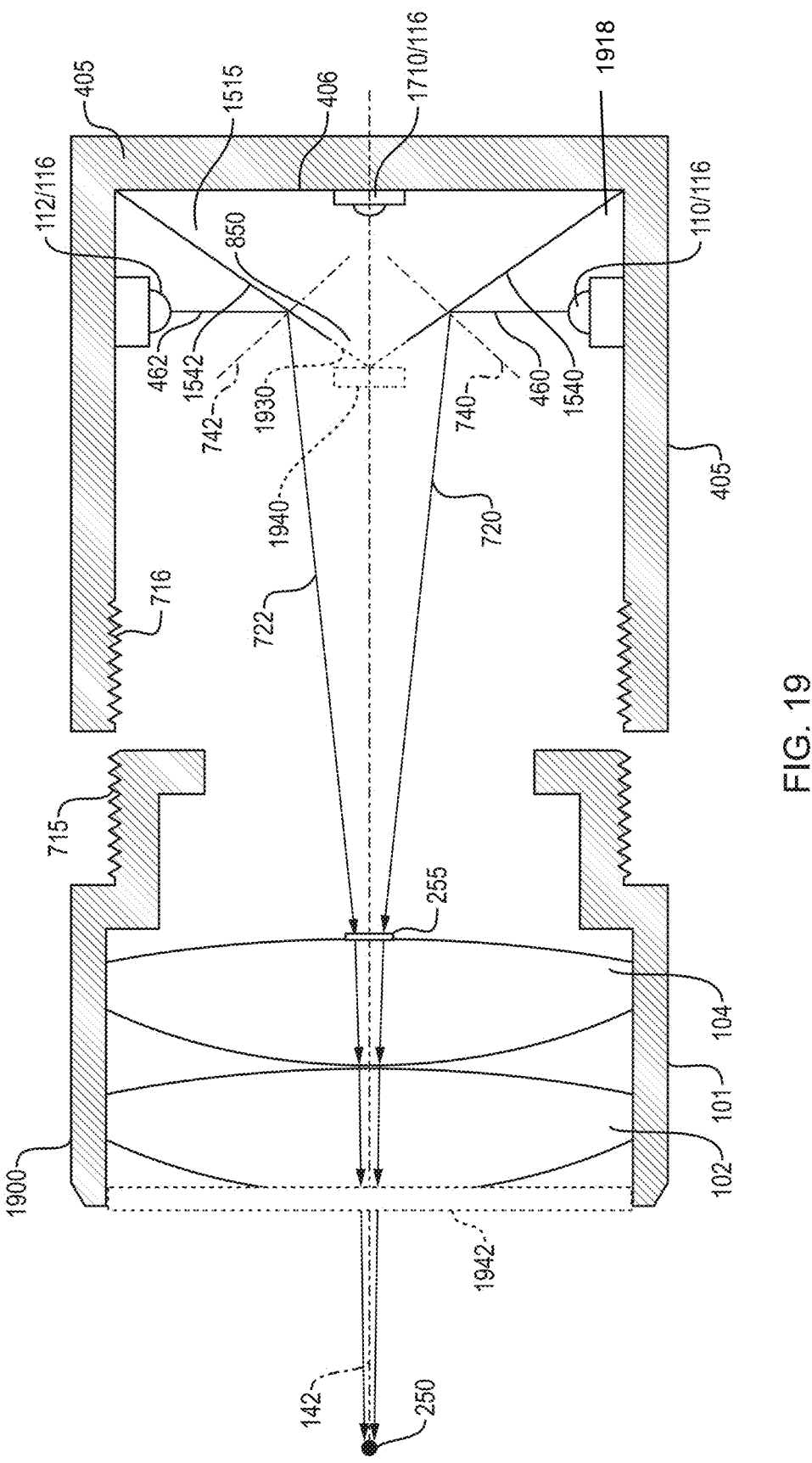
FIG. 19 illustrates a cut-away side view of a further aspect of the exemplary embodiment of a lighting devices shown herein.

FIG. 19 illustrates a cut-away side view of a further aspect of the exemplary embodiment of a lighting device shown, herein, (e.g., FIGS. 4B, 8A and 8B).

In accordance with this aspect of the invention, which is comparable to the embodiment, lighting device 1900 comprises lens assembly 101 and lighting assembly 1918, comprising light director 1515 and a plurality of lighting sources 110, 112 (or lighting modules 110/116, 112/116). In accordance with this aspect of the invention, light director 1515 comprises a plurality of reflective surface 1540, 1542 arranged at an apex angle 850 wherein in one aspect of the invention, the apex angle is greater than 90 degrees.

An understanding and more detailed description of the aspect of this invention may be obtained from a reading of the disclosure with regard to FIGS. 4B, 8A, 8B, etc.

In addition, in this aspect of the invention, reflective surfaces 1540, 1542 fail to meet at their apex. Rather, surfaces 1540, 1542 are sized to create a gap 1930 at their apex through which light may pass.

Further illustrated is an additional lighting source 1710 (module 1710/116) positioned on base 405. As previously discussed with regard to FIG. 17, lighting source 1710 is configured to emit a light along optical axis 142 formed by lens 102, 104. In this illustrated example, light emitted by lighting source 1710 passes unaltered through gap 1930 to project light onto region 255.

In accordance with the principles of the invention, light emitted by lighting sources 110, 112, and 1710 may be combined within region 255, wherein the combined light is focused onto point (i.e., object, plane) 250, as previously disclosed.

In one aspect of the invention, lighting source 1710 may emit a white light and lighting sources 110, 112 may emit light in one or more colored light wavelength bands (i.e., non-white) or non-visible wavelength band. For example, although lighting source 110 has been described with regard to emitting a white light, in the previously discussed devices, it would be understood that the disclosed light emitted by lighting sources 110, 112, 114, 1710, 1712 may be altered without altering the scope of the invention claimed.

For example, lighting source 1710 may emit a white light and lightings sources 110, 112 may emit a same colored light (e.g., blue light, green light, red light, etc.), or may emit light within a same color wavelength band at different wavelengths or within different colored light wavelength bands. Or lighting source may emit light in a colored wavelength band and lighting sources 110, 112 may emit light in a same or different colored wavelength band.

In one aspect of the invention, lighting device 1900 may further comprise one or more filter elements 1940 (1942) that may be used to limit one or more wavelength ranges emitted by lighting device 1900 similar to that discussed with regard to FIGS. 17 and 18, for example. In one aspect of the invention filter 1940 may be inserted within, or proximate to, gap 1930 between reflective surfaces 1542, 1544. In this configuration, light emitted by lighting source 1710 may be limited in a desired wavelength range. For example, blue light wavelength range or limited white light wavelength range similar to that shown in FIG. 18.

Alternatively, filter 1942 may be inserted in a distal end of lens assembly 101. In this alternative configuration, light emitted by the combination of lighting sources 1710, 110, 112, etc., may be limited to one or more known wavelength ranges (e.g., see FIG. 18).

Figure 20:
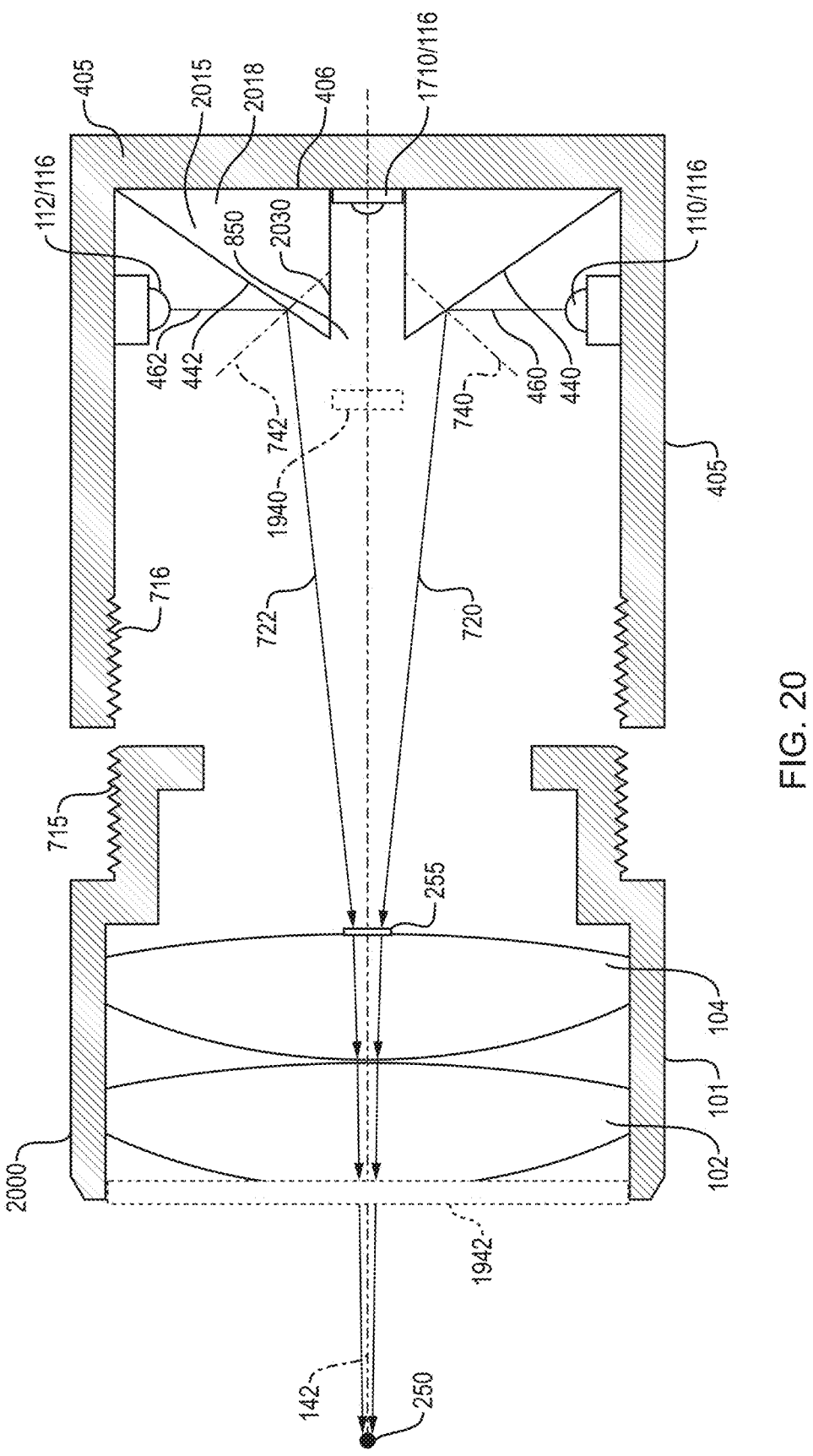
FIG. 20 illustrates a cut-away side view of a further aspect of the exemplary embodiment of a lighting device shown herein.

FIG. 20 illustrates a cut-away side view of a further aspect of the exemplary embodiment of a lighting device shown in FIG. 8A.

In this exemplary aspect of the invention, lighting device 2000 including lens assembly 101 and housing 405, which includes lighting assembly 2018 comprising lighting sources 110, 112 (modules 110/116, 112/116) positioned on an inner surface associated with lighting assembly 2018 and lighting module 1710/116 positioned on base 406, similar to the configuration shown in FIG. 19.

Further illustrated is light director 2015, which similar to light director 815, previously discussed, comprises reflective surfaces 440, 442 orientated at an angle with respect to base 405, wherein reflective surfaces 440, 442 are directed to merge at an apex. However, in this aspect of the invention, light director 2015 further comprises passage or tunnel 2030, extending from the illustrated apex to base 406, wherein light emitted by lighting module 1710/116 passes to lens 102, 104.

In one aspect of this configuration, light director 2015 operates in a manner similar to that discussed with regard to light director 815 and 1515 (see FIGS. 4B, 8A, 8B, etc.,) in that light from lighting sources 110, 112 is reflected by reflective surfaces 442, 444 toward region 255 and light emitted by lighting source 1710 is directed to region 255 on lens 104, 102 along optical axis 142. The combined light may converge onto point 250 in a manner as previously discussed.

Further illustrated are optional, filters 1940, 1942 that limit a wavelength range of the light emitted by lighting device 2000 as discussed previously.

Figure 21A:
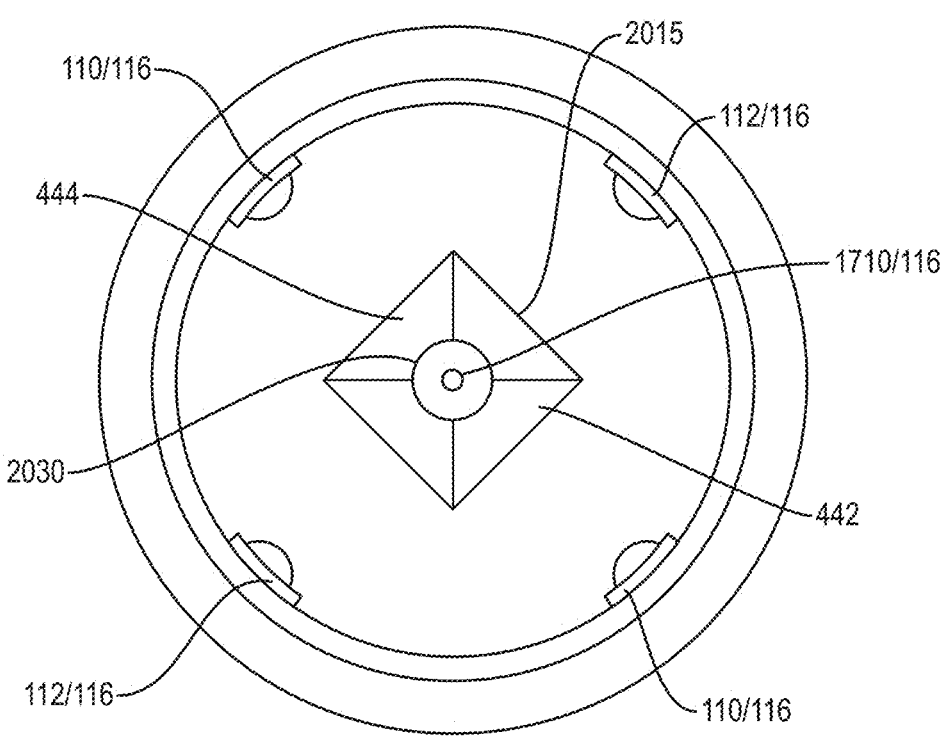
FIGS. 21A, 21B illustrated exemplary aspects of the invention as discussed in FIG. 20.
Figure 21B:
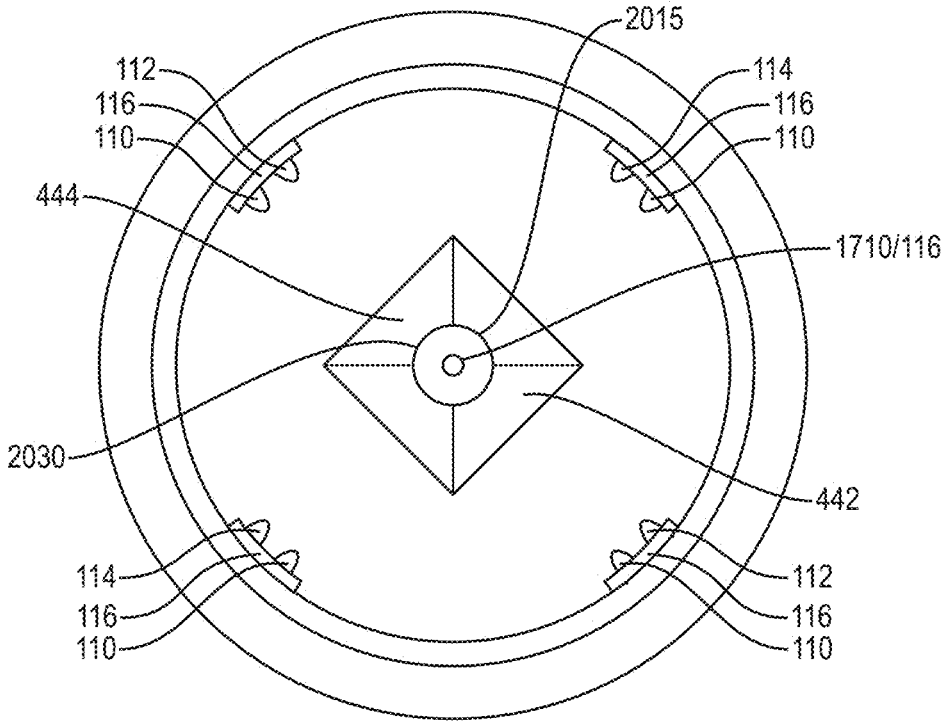

FIGS. 21A, 21B illustrated exemplary aspects of the invention discussed in FIG. 20.

FIG. 21A illustrates a front view of the first aspect of the lighting device shown in FIG. 20.

In this illustrated aspect, a plurality of lighting sources 110, 112 (or lighting modules 110/116, 112/116) are arranged about an inner circumference surface of lighting assembly 2018 in a first plane.

Light emitted by lighting sources 110, 112 (concurrently, individually or sequentially) is directed toward light director 2015, which redirects the light toward lens assembly 101 (not shown), as previously discussed.

Further illustrated is lighting source 1710 (or lighting module 1710/116) viewable through passage 2030 within light director 2023. Lighting source 1710 emits light along optical axis 142 (not shown as it extends into the plane of the page the drawing is on) toward lens assembly 101 as previously discussed. Although only four lighting sources 110, 112 (or lighting module 110/116, 112/116) are shown, it would be recognized that the number of lighting modules included along the inner surface of lighting assembly 2018 may be increased or decreased based on the number of reflective surfaces of light director 2015. In addition, although a single lighting source 1710 is discussed, it would be understood that lighting source 1710 (and lighting sources 110, 112, 114) may comprise an array of lighting sources that may emit light in one of: a same or a different wavelength band.

FIG. 21B illustrates a front view of a second aspect of the lighting device shown in FIG. 20.

In this exemplary aspect, a plurality of lighting sources 110 and 112 (or lighting modules 110/116, 112/116) arranged as pairs about an inner circumference surface of lighting assembly 2018, wherein the lighting source pair 110/112 are controlled by a same controller 116.

In this exemplary aspect, light emitted by lighting sources 110, 112 (concurrently, individually or sequentially) is directed toward light director 2015, which redirects the light toward lens assembly 101 (not shown), as previously discus.

Although only four lighting modules are shown, it would be recognized that the number of lighting modules included along the inner surface of lighting assembly 2018 may be increased or decreased based on the number of reflective surfaces of light director 815.

Although the lighting devices discussed have been described with regard to two lighting sources or modules, it would be understood that the multi-source lighting configurations shown, herein, may include a plurality of lighting sources suitable for emitting light of different light wavelength ranges (e.g. UV, violet, blue, green, yellow, orange, red, IR, etc.).

Figure 22:
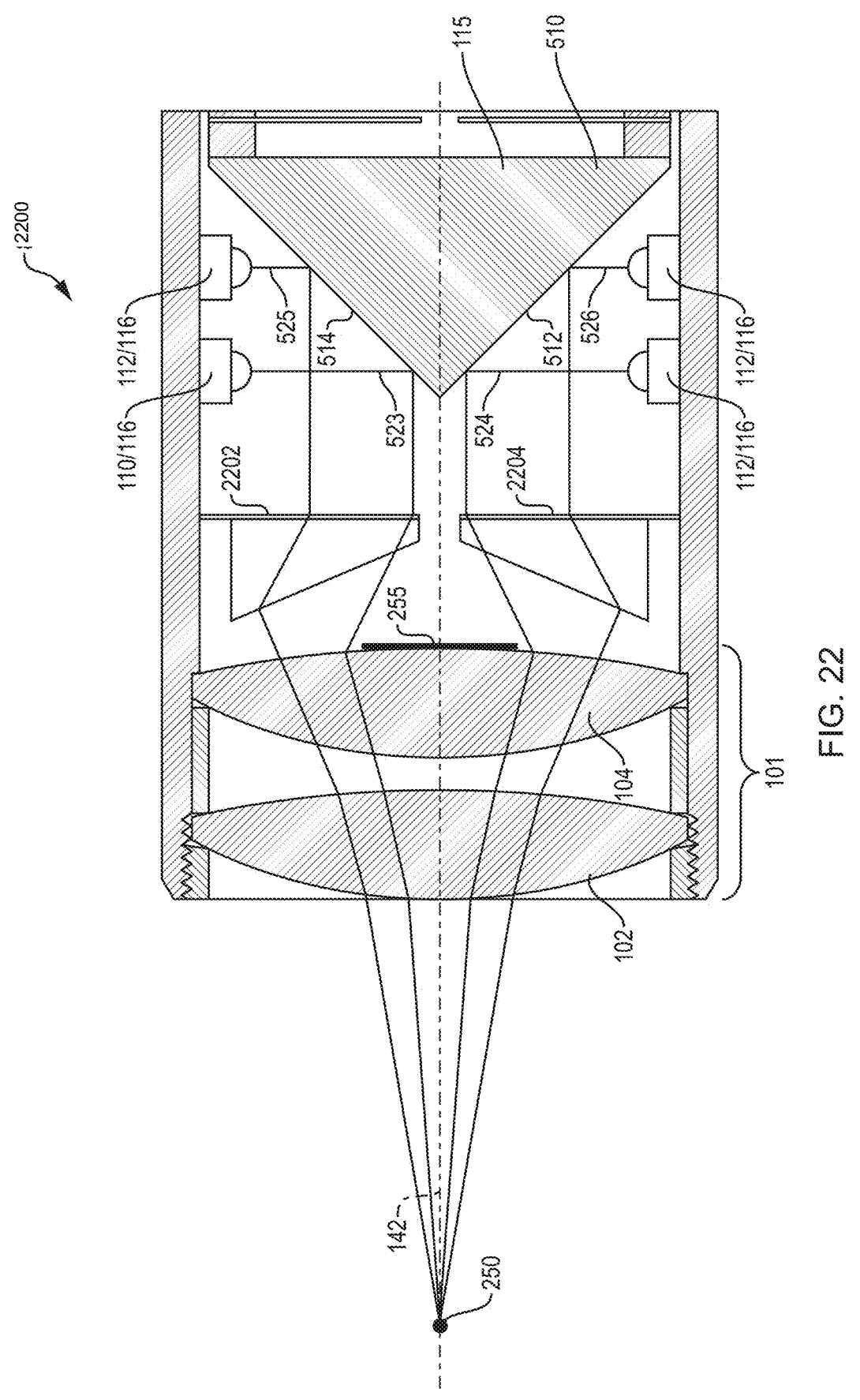
FIG. 22 illustrate still further exemplary embodiments of a lighting elements in accordance with the principles of the invention.

FIG. 22 illustrates an eighth exemplary embodiment of a lighting element 2200, wherein wedge prisms 2202, 2204 are incorporated into the path of light redirected by lighting director 510. Wedge prisms 2202, 2204 provide for the divergence of the light emitted by lighting sources 110, 112, such that the region 255 on lenses 102, 104 is increased. As would be understood from the disclosure presented, herein, the power of lenses 102, 104 may be adjusted and/or determined using the method described to obtain converges of the light onto common point 250.

In accordance with the principles of the invention, the light emitted by lighting sources or modules disclosed herein may be emitted individually or concurrently, the intensity of the light emitted by the lighting sources may be the same or different. As an example, with the emission of a single white light, the light intensity may be set to a known value (e.g., maximum), whereas the light intensity of the white light source may be reduced when a non-white light is concurrently emitted.

Although specific wavelength ranges are discussed above, it would be recognized that the wavelength ranges are merely representative of light wavelength ranges as different sources may quote different specific values for the disclosed color wavelength ranges.

In summary, a lighting device is disclosed, which comprises a plurality of lighting modules or sources arranged at an angle from an optical axis of a lens assembly, wherein the light is directed toward a lens assembly in a manner that allows for the convergence by the optical powers of the lenses within the lens assembly of the light from the plurality of lighting sources. In a second embodiment, a lighting device is disclosed comprising a plurality of lighting modules or sources arranged along an inner circumference surface of the device house and the light generated by the lighting sources is directed to a device for redirecting the light toward a lens assembly wherein the optical power of the lenses allows for the convergence of the light from the plurality of lighting sources to a desired point.

In accordance with one aspect of the principles of the invention, the light director, receiving light from the lighting modules or sources, may be configured to re-direct the light to a known region on the lens assembly to enable the re-directed light to converge to a known point after passing through at least one projection (or objective) lens. In accordance with another aspect of the invention, the lighting sources may be oriented with respect to the light director such that the light emitted by the lighting sources are re-directed by the light director such that the re-directed light is focused onto a known point on the objective lens.

In accordance with the principles of the invention, a lighting device may be incorporated into a lighting assembly that provides light at greater light intensity at a same wavelength or at one or more different wavelengths or in one or more different wavelengths bands, wherein the emitted light is directed toward or focused onto a common point such that the common point is of a higher intensity.

In one aspect of the invention, a single light assembly may contain lighting devices disclosed herein, wherein the light assembly is suspended from an eyewear, a headband or a head-strap and emits light of a greater intensity in one or more wavelength bands. For example, the lighting devices may emit light concurrently or separately emit light in a non-visible (i.e., ultra-violet, infra-red) wavelength range and in a visible wavelength range (e.g., white or non-white (e.g., blue, green, etc.), wherein the emitted light is directed toward a common point such that the light at the common point is of a higher intensity.

In one aspect of the invention, the lighting devices disclosed herein may be incorporated into a dual lighting assembly, wherein the lighting assembly is suspended from an eyewear, a headband or a head-strap and emits light of a greater intensity in one or more wavelength bands.

For example, one lighting device of the dual lighting assembly may emit light in a first wavelength band (e.g., non-visible) and the second lighting device may emit light is a visible wavelength band (e.g., white, non-white) toward a common point such that the light at the common point is of a higher intensity. Alternatively, each of the lighting devices within the dual lighting assembly may light in both a visible and a non-visible wavelength band toward a common point such that the light at the common point is of a higher intensity. The light emitted by each of the lighting devices may be emitted concurrently or separately in one or more of a non-visible wavelength range or a visible wavelength range. In addition, the intensity of the light emitted by each lighting source within a corresponding lighting device may be varied during the emission of light.

In still another aspect of the invention, the lighting devices disclosed herein may be incorporated into a triple (or plurality of) lighting assembly, wherein the lighting assembly is suspended from an eyewear, a headband or a head-strap and emits light of a greater intensity in one or more wavelength bands.

For example, one lighting device of the triple lighting assembly may emit light in at a first wavelength in first wavelength band (e.g., non-visible), a second lighting device may emit light is a visible wavelength band (e.g., white, non-white) and a third lighting device may emit light at a second wavelength within the first wavelength band, wherein the light from each of the lighting device is directed toward a common point such that the light at the common point is of a higher intensity. Alternatively, each of the lighting devices within the triple lighting assembly may emit light in both a visible and a non-visible wavelength band toward a common point such that the light at the common point is of a higher intensity. The light emitted by each of the lighting devices may be emitted concurrently or separately in one or more of a non-visible wavelength range or a visible wavelength range. In addition, the intensity of the light emitted by each lighting devices within a corresponding lighting element may be varied during the emission of light.

In still another embodiment of the invention, a visualization system may be formulated from the combination of an eyewear with the previously discussed lighting assemblies, wherein the lighting assemblies may be suspended from the eyewear, a headband or a head-strap. The lighting assembly (comprising single, dual or triple lighting devices) may emit light in one or more wavelength bands and the eyewear which includes carrier lens may include a filter system, either within the carrier lens or external to the carrier lens, wherein the filter system may cause the attenuation of light viewed by a user in a selected wavelength band while allowing light in another wavelength band to pass substantially unattenuated (i.e., almost zero attenuation.

In a still further embodiment of the invention, a visualization system may be formulated from the combination of an eyewear with the previously discussed lighting assemblies, wherein the lighting assemblies may be suspended from the eyewear, a headband or a head-strap. The lighting assembly (comprising single, dual or triple lighting devices) may emit light in one or more wavelength bands and the eyewear which includes carrier lens may include a filter system, either within the carrier lens or external to the carrier lens, wherein the filter system may cause the attenuation of light viewed by a user in a selected wavelength band while allowing light in another wavelength band to pass substantially unattenuated (i.e., almost zero attenuation of the light). In addition, a magnification device may be incorporated into each of the carrier lens, wherein the magnification devices provide for an enlarged view of an area around the common point about which the emitted light is directed toward or focused onto.

In one aspect of the invention, the magnification devices may include a filtering system wherein the filtering system may cause the attenuation of light viewed by a user in a selected wavelength band while allowing light in another wavelength band to pass substantially unattenuated (i.e., almost zero attenuation). In one aspect the filtering system may comprise a first filter configured to filter light entering the magnification devices such that the light in a first wavelength band may be reduces in magnitude or intensity while allowing light in a second wavelength to pass substantially unattenuated (i.e., almost 100 percent of the light passes). The filtering capability of the first filter may be determined based on the intensity or magnitude of the incoming light. The filtering system further comprising a second filter, having optical properties to filter the light passing through the magnification device (and been magnified), based on the magnification level of the magnification devices and the optical properties of the first filter. The second filter configured to further reduce in magnitude the light in the first wavelength range while allowing light in a second wavelength range to pass substantially unattenuated.

Although the invention has been described with regard to a lighting source, in a preferred embodiment the lighting sources are light emitting diodes (i.e., LEDs), it would be understood that other lighting sources may be incorporated into the invention disclosed without undue modification and, thus, considered within the scope of the invention claimed.

In addition, while the term "lighting module" or "lighting source" has been described with regard to "light emitting diode," it would be recognized that the term "a light emitting diode" may comprise a plurality of light emitting diode elements arranged in one of a matrix or circular pattern. Furthermore, the plurality of light emitting diodes may be within a base dimension of the disclosed dome lens and the positioning of the at least one light emitting diode within a focal length of the dome lens is advantageous as it defocuses and blurs the distinction of the light emitted by the individual light emitting diodes within the array or circular pattern.

Furthermore, the light emitted or output by the light emitting diode(s) is referred to being within a frequency or wavelength range, wherein the wavelength range represents a color (e.g., blue light approximately 400 nanometers to 450 nanometers). However, it would be further understood that light, particularly with regard to light emitting diodes, may be measured in color temperature, as degrees Kelvin. For example, a soft white light may be measured in a range of 2700° K-3000° K whereas a bright white light may be expressed in a range of 5000° K-6000° K.

Hence, one of ordinary skill in the art would appreciate that the reference to light or emitted light may be measured as frequency, wavelength, color or color temperature, and such terminology of light is incorporated and used interchangeably, herein.

One of ordinary skill in the art will further recognize and appreciate that various modifications and changes can be made without departing from the scope of the invention as set forth in the claims. Accordingly, the specification is to be regarded in an illustrative manner, rather than with a restrictive view, and all such modifications are intended to be included within the scope of the invention.

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instance, the terms "about" may include numbers that are rounded (or lowered) to the nearest significant figure. Furthermore, the values presented herein are merely to illustrate the concepts and are not to be considered as the only values that have been contemplated and considered.

Although the terms "perpendicular" and "orthogonal" are used herein to describe a relationship between two elements, it would be understood and recognized by those skilled in the art that the terms "perpendicular" and "orthogonal" are not used in the mathematical sense (i.e., precisely ninety (90) degrees). But rather in the manufacturing sense wherein a tolerance value is imposed. Such tolerance values may be considered, for example, +/−1 degree. Thus, the terms "substantially perpendicular, "substantially "orthogonal," "substantially center," etc. should be understood as being used to represent a relationship between elements in the manufacturing sense (i.e., within known tolerance values).

Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

It is expressly intended that all combinations of those elements that perform substantially the same function in substantially the same way to achieve the same results are within the scope of the invention. Substitutions of elements from one described embodiment to another are also fully intended.

What is claimed is:

1. A lighting device comprising:
   a lens assembly comprising:
      at least one objective lens, the at least one objective lens forming an optical axis; and
   a housing containing therein:
      a plurality of lighting sources positioned about an inner circumference of the housing; and
      a prismatic structure comprising:
         a plurality of reflective surfaces extending from a base of the housing, wherein a corresponding one of the plurality of reflective surfaces being positioned opposite a corresponding one of at least one of the plurality of lighting sources, the prismatic structure configured to:
            receive light emitted by corresponding ones of the plurality of lighting sources; and re-direct the received light emitted by the lighting sources toward the at least one objective lens, within the lens assembly; and direct the re-directed light onto the least one objective lens, wherein an optical power of the combination of the at least one objective lens of the lens assembly being selected to focus the light onto an area a known distance from lens assembly.

2. The lighting device of claim 1, wherein lighting sources are configured to:

emit a white light.

3. The lighting device of claim 2, comprising:

a filter positioned between selected ones of the plurality lighting sources and a corresponding reflective surface, the filter configured to:

limit the light emitted by the lighting sources to a known wavelength range.

4. The lighting device of claim 1, wherein the optical characteristics of the at least one lens is based on a distance between an apex of the prismatic structure and the at least one lens.

5. The lighting device of claim 1, wherein a gap is formed between the reflective surfaces at an apex of the prismatic structure.

6. The lighting device of claim 5, comprising:

a lighting source positioned on the base of the housing, the lighting source configured to emit light through the gap at the apex of the prismatic structure.

7. The lighting element of claim 1, wherein the plurality of reflective surfaces form a multi-sided structure.

8. The lighting device of claim 7, wherein the multi-sided structure comprises:

at least a 3-sided pyramid.

9. The lighting device of claim 1 comprising:

a filter positioned on a distal end of the housing, the filter configured to:

limit a range of wavelengths emitted by the lighting element.

10. The lighting device of claim 1 wherein selected ones of the plurality of lighting sources are configured to:

emit light in a known wavelength band.

11. The lighting device of claim 10, wherein selected other ones of the plurality of lighting sources are configured to:

emit light in a second known wavelength band.

12. The lighting device of claim 11, wherein intensity of the light emitted in in the known wavelength band and the second known wavelength band may be the same or different.

13. The lighting device of claim 10, wherein a wavelength of light emitted by the selected ones of the plurality of lighting sources in the known wavelength band may be the same or different.

14. The lighting device of claim 11, wherein a wavelength of light emitted by the selected other ones of the plurality of lighting sources in the second known wavelength band may be the same or different as those in the first known wavelength band.

15. The lighting device of claim 1, wherein the reflective surface are arranged to form an apex, the apex possessing an apex angle between the reflective surface selected from the group comprising: greater than ninety (90) degrees, substantially ninety (90) degrees and less than ninety (90) degrees.

16. The lighting device of claim 15, wherein a gap is formed at the apex.

17. The lighting device of claim 16 comprising:

a lighting source positioned on the base, wherein light emitted by the lighting source positioned on the base is emitted along the optical axis through the gap.

18. The lighting device of claim 15, wherein the plurality of lighting elements are arranged about the inner circumference substantially perpendicular to the optical axis and the apex angle is less than ninety (90) degrees.

19. A lighting device comprising:

a lens assembly comprising:

at least one objective lens, the at least one objective lens forming an optical axis; and a housing containing therein:

a plurality of lighting sources positioned about an inner circumference of the housing, wherein the plurality of lighting sources are arranged substantially perpendicular to the optical axis; and a prismatic structure comprising:

a plurality of reflective surfaces extending from a base of the housing, wherein the corresponding ones of the plurality of reflective surfaces are positioned opposite a corresponding one of at least one of the plurality of lighting sources, wherein the reflective surfaces are arranged to form an apex having an apex angle between the reflective surfaces less than ninety (90) degrees, the prismatic structure configured to:

receive light emitted by corresponding ones of the plurality of lighting sources; and re-direct the received light emitted by the lighting sources toward the at least one objective lens within the lens assembly, wherein an optical power of the at least one objective lens being selected to focus the light onto an area a known distance from lens assembly.

20. The lighting device of claim 19, wherein the optical power of the at least one objective lens is selected to achieve a desired light of light intensity in the area.

* * * * *